(12) United States Patent
Ascher et al.

(10) Patent No.: US 7,790,749 B2
(45) Date of Patent: Sep. 7, 2010

(54) **USE OF PLEUROMUTILINS FOR THE TREATMENT OF DISORDERS CAUSED BY *HELICOBACTER PYLORI***

(75) Inventors: Gerd Ascher, Kundl (AT); Johannes Hildebrandt, Oeynhausen (AT)

(73) Assignee: Nabriva Therapeutics AG, Vienna (AT)

( * ) Notice: Subject to any disclaimer, the term of this patent is extended or adjusted under 35 U.S.C. 154(b) by 921 days.

(21) Appl. No.: 10/510,532

(22) PCT Filed: Apr. 22, 2003

(86) PCT No.: PCT/EP03/04173

§ 371 (c)(1), (2), (4) Date: Oct. 7, 2004

(87) PCT Pub. No.: WO03/090740

PCT Pub. Date: Nov. 6, 2003

(65) Prior Publication Data

US 2005/0131023 A1    Jun. 16, 2005

(30) Foreign Application Priority Data

Apr. 23, 2002    (GB) ................................. 0209262.5

(51) Int. Cl.
*A01N 43/40* (2006.01)
*A01N 33/00* (2006.01)
*A01N 47/28* (2006.01)

(52) U.S. Cl. .................. 514/319; 514/579; 514/588

(58) Field of Classification Search ............... 514/319, 514/579, 588
See application file for complete search history.

(56) References Cited

U.S. PATENT DOCUMENTS 4,675,330 A    6/1987    Berner et al. ............... 514/365

6,303,572 B1    10/2001    Rowe ............................ 514/6
2004/0235784 A1    11/2004    Jomaa et al. ................. 514/50

FOREIGN PATENT DOCUMENTS

| CA | 2042138 | 11/1992 |
|----|---------|---------|
| EP | 0 153 277 | 8/1985 |
| WO | 99/00136 | 1/1999 |
| WO | 01/09095 | 2/2001 |
| WO | 02/04414 | 1/2002 |
| WO | 02/22580 | 3/2002 |

OTHER PUBLICATIONS

De Luis et al. Association of *Helicobacter pylori* infection with cardiovascular and cerebrovascular disease in diabetic patients. Diabetes Care, vol. 21, No. 7, Jul. 1998.*

Dornheim, et al.; "The Effects of Tiamulin, a Semisynthetic Pleuromutilin Derivative, on Bacterial Polypeptide Chain Initiation;" *European Journal of Biochemistry*; vol. 91, No. 2, pp. 465-473 (1978).

Kavanagh, F., et al.; "Antibiotic Substances From Basidiomycetes. VIII. Pleurotus Mutilus (Fr.) Sacc. and Pleurotus Passeckerianus Pilat;" *Proc. N.A.S.*; Department of Botany, Columbia University and The New York Botanical Garden; pp. 570-574 (1951).

Malfertheiner, P., et al.; "Current concepts in the management of *Helicobacter pylori* infection—The Maastricht 2-2000 Consensus Report;" *Alimentary Pharmacology & Therapeutics*; vol. 26, Issue 2, pp. 167-180 (2002).

Rokkas, T.; "Treatment of *H. pylori* infection: Current recommendations;" *Annals of Gastroenterology*; vol. 18, No. 2, pp. 119-126 (2005).

Shinohara, et al.; "Gastric Diseases Related to *Heliobacter pylori* and Epstein-Barr Virus;" *Microbiology and Immunology*; vol. 42, No. 6, pp. 415-421.

* cited by examiner

*Primary Examiner*—Sreeni Padmanabhan
*Assistant Examiner*—Renee Claytor
(74) *Attorney, Agent, or Firm*—D. Peter Hochberg; Sean F. Mellino; Daniel J. Smola

(57) ABSTRACT

A method of preventing or treating diseases mediated by *Helicobacter pylori*, comprising administering to a subject in need of such treatment an effective amount of pleuromutilin.

3 Claims, No Drawings

USE OF PLEUROMUTILINS FOR THE TREATMENT OF DISORDERS CAUSED BY *HELICOBACTER PYLORI*

The present invention relates to *Helicobacter pylori* treatment, such as treatment of diseases mediated by *H.pylori*, with pleuromutilins.

Infections with *Helicobacter pylori* may contribute to diseases such as active chronic gastritis, peptic ulcer disease and gastric adenocarcinoma, and are also reported to contribute e.g. to malignant lymphoma of mucosa-associated lymphoid tissue of the stomach, chronic renal failure, HIV, pernicious anemia, Zollinger-Ellison syndrome, choleric polyps. Pharmaceuticals which are currently used in the treatment of *H.pylori* infections include antimicrobials, such as tetracycline, amoxicillin, metronidazole, clarithromycin, and mixtures of proton-pump inhibitors, such as omeprazole or lansoprazole, together with a second antimicrobial, e.g. amoxicillin or clarithromycin, but a major problem is the appearance of *H. pylori* strains which have become resistant to one ore several of the above mentioned antibiotics.

We have now surprisingly identified a compound class which shows surprisingly antibacterial activitiy in vitro against *H. pylori*, and which may be useful in the treatment of diseases mediated, e.g. caused, by *H. pylori*, e.g. even in against drug resistant strains.

In one aspect the present invention provides the use of a pleuromutilin in the preparation of a medicament for the treatment of diseases mediated by *Helicobacter pylori*.

In another aspect the present invention provides a method for the treatment of diseases mediated by *Helicobacter pylori*, comprising administering to a subject in need of such treatment an effective amount of a pleuromutilin.

Diseases mediated by *H.pylori* or *H.pylori* infections include e.g. active chronic gastritis, peptic ulcer disease, gastric adenocarcinoma, malignant lymphoma of mucosa-associated lymphoid tissue of the stomach, chronic renal failure, HIV, pernicious anemia, Zollinger-Ellison syndrome, choleric polyps, e.g. which diseases are found simultanously.

A pleuromutilin for treatment includes one or more pleuromutilins, e.g. a combination of different pleuromutilins. Treatment includes treatment and prophylaxis. A pleuromutilin of the present invention includes a pleuromutilin in the form of a free base, and, where existing, in the form of a salt, in the form of a solvate and in the form of a salt and a solvate, e.g. and in the form of a complex, such as a cyclodextrin complex.

A pleuromutilin of the present invention may exist in the form of isomers and mixtures thereof, e.g. including diastereoisomers and mixtures thereof. Isomeric mixtures may be separated as appropriate, e.g. according to a method as conventional, to obtain pure isomers. The present invention includes a pleuromutilin according to the present invention in any isomeric form and in any isomeric mixture, such as described in patent literature cited below, which patent literature is introduced herein by reference with respect to isomeric forms of pleuromutlins. Preferably the configuration in the mutilin ring is the same as in a naturally produced mutilin.

A pleuromutilin for use according to the present invention or for treating diseases according to the present invention is designated hereinafter as "a pleuromutilin(s) of (according to) the present invention".

Pleuromutilin, a compound of formula

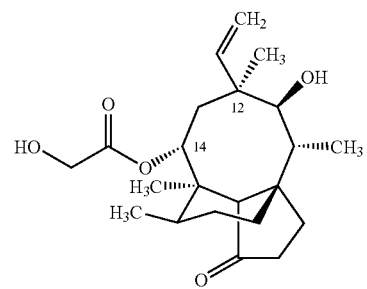

A is a naturally occurring antibiotic, e.g. produced by the basidomycetes Pleurotus mutilus and *P.passeckerianus*, see e.g. The Merck Index, 12th edition, item 7694.

A number of further pleuromutilins having the principle ring structure of pleuromutilin and having e.g. antibacterial activity, have been developed.

A pleuromutilin of the present invention includes a pleuromutilin having the basic structural elements as set out in formula

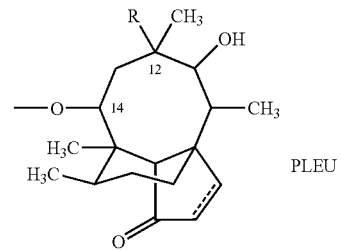

PLEU wherein R is vinyl or ethyl and the dotted line is a bond or is no bond.

The following numbering system is used in the present application:

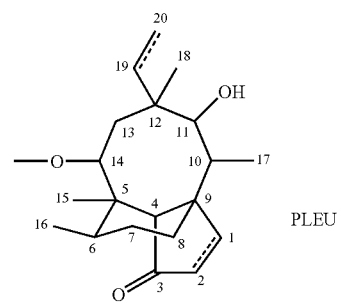

PLEU

The dotted line between positions 19 an 20 (and between positions 1 and 2) is a bond or is no bond. In a compound of formula A or of formula PLEU a hydrogen atom in positions 4, 7 and/or 8 of the ring system may be replaced by deuterium, and if the dotted line between positions 1 and 2 is no bond (single bond between positions 1 and 2) the ring system may be further substituted in positions 1 and/or 2, e.g. by halogen, deuterium or hydroxy. The group —O— in position 14 is further substituted, preferably by a substituted carbonyl group.

Examples of pleuromutilins according to the present invention includes e.g.

A compound as disclosed in U.S. Pat. No. 3,716,579, e.g. of formula

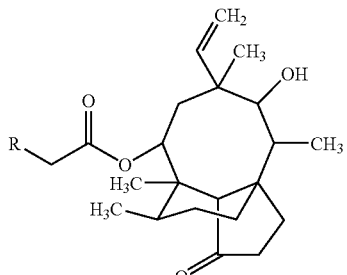

I-U.S. Pat. No. 3,716,579 wherein R is $CH_3$—$(CH_2)_7$—CH=CH—$(CH_2)_7$—COO—, $CH_3$—$(CH_2)_4$—CH=CH—$CH_2$—CH=CH—$(CH_2)_7$—COO—, $CH_3$—$(CH_2)_9$—CH=CH—$(CH_2)_7$—COO— or hydrogen;

A compound as disclosed in GB1312148, e.g. of formula

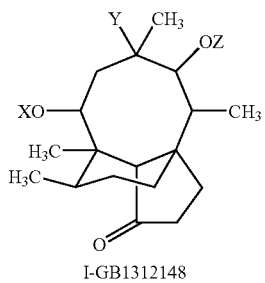

I-GB1312148 wherein X, Y and Z are as defined in any one of the following groups:

a. X is —CO—$CH_2$—$R_1$, wherein $R_1$ is H, Cl, Br, I, thiocyanato, azido, (N,N-tetramethylene-thiocarbamoyl)-mercapto, dithiocarbonic acid-O—$(C_{1-3})$alkyl, —S-phenyl, S-phenyl substituted by carboxyl or by one or two OH, —S-pyridyl, —S-benzyl, —S—$(C_{1-5})$alkyl, or —S—$(C_{1-5})$alkyl substituted by one or more amino, OH or carboxyl, Y is vinyl, and Z is H;
b. X is —CO—CO—OH, Y is vinyl and Z is H;
c. X is —$COCH_3$, Y is vinyl and Z is H;
d. X is $COCH_2NH_2$, Y is ethyl and Z is H;
e. X is a group of formula

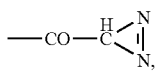

Y is ethyl and Z is H
f. X is H, Y is vinyl and Z is acetyl; or
g. X is $COR_2$, wherein $R_2$ is $(C_{1-5})$alkyl, Y is vinyl and Z is H, A compound as disclosed in U.S. Pat. No. 4,278,674, e.g. of formula

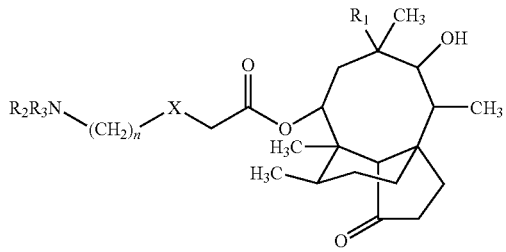

I-U.S. Pat. No. 4,278,674 wherein $R_1$ is vinyl or ethyl, n is an integer from 2 to 5, X is sulphur or a group —Y— phenylene-Z— or a group =$NR_4$, Y and Z are both sulphur or one of Y and Z is sulphur and the other is oxygen, $R_4$ is H or a second mutilin ring of formula I-U.S. Pat. No. 4,278,674, wherein $R_1$ is as defined above and attached via a —O—CO—$CH_2$— group in position 14; each of $R_2$ and $R_3$ are (independently of each other) $(C_{1-10})$alkyl, or $R_2$ and $R_3$ together with the nitrogen atom form pyrrolidino, piperidino, morpholino, thiomorpholino, or 1-hexahydro-1H-azepino, or $R_2$ and $R_3$ together with the nitrogen atom form piperazinyl, the second nitrogen atom of which is substituted by $(C_{1-5})$alkyl, $(C_{1-4})$hydroxyalkyl, $(C_{2-5})$alkynoyloxy$(C_{1-4})$alkyl, or benzoyloxy$(C_{1-4})$alkyl, or $R_1$ is as defined above, n=2, $R_3$ is $(C_{1-10})$alkyl, $(C_{1-4})$hydroxyalkyl, $(C_{2-5})$alkynoyloxy-$(C_{1-4})$alkyl, or benzoyloxy$(C_{1-4})$alkyl, X is =$NR'_4$ and $R_2$ together with $R'_4$ forms an ethylene bridge between both nitorgen atoms; such as 14-Desoxy-14[(2-diethylaminoethyl)mercaptoacetoxy] mutilin, e.g. also known as tiamulin of formula

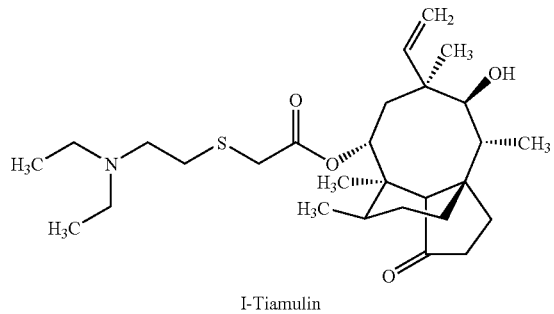

I-Tiamulin

A compound as disclosed in U.S. Pat. No. 4,130,709, e.g. of formula

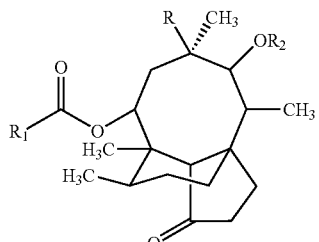

I-U.S. Pat. No. 4,130,709 wherein R is ethyl or vinyl, $R_1$ is selected from α- or β-anomers of hexopyranoses, hexofuranoses, pentopyranoses, pentofuranoses, pyranose and furanose aminosugars, disaccharides, trisaccharides and $R_2$ is H, benzoyl or $(C_{2-4})$alkanoyl; or $R_1$ is 2-deoxy-2-(hydroxyimino)-3,4,6-tri-O-acetyl-α-D-glucopyranosyl or -galactopyranosyl, 2-deoxy-2-(hydroxyimino)-α-D-galactopyranosyl, 2-deoxy-2-amino-4,6-di-O-acetyl-α-D-glucopyranosyl, or 2-deoxy-2-acetamido-3,4,6-tri-O-acetyl-α-D-glucopyranosyl and $R_2$ is H;

A compound as disclosed in U.S. Pat. No. 4,129,721; e.g. of formula

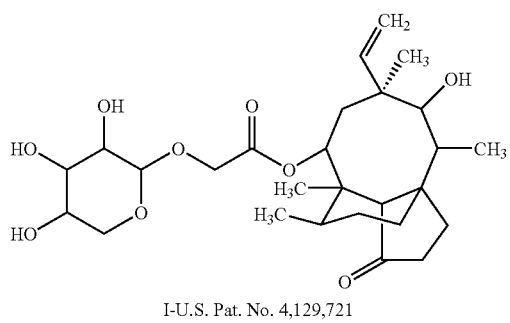

I-U.S. Pat. No. 4,129,721 and the 19,20-dihydro derivative thereof and the tetra $(C_{2-6})$alkanoyl derivatives thereof;

A compound as disclosed in EP0013768, e.g. of formula

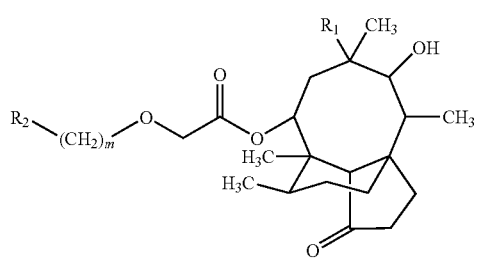

I-EP0013768 wherein $R_1$ is vinyl or ethyl, m is 0 or 1, and $R_2$ is a heterocyclic radical, in which a 5- or 6-membered, unsaturated or saturated heterocyclic ring containing one or more hetero atoms selected from O, S and N, is attached to the —$S(CH_2)_m$— group;

A compound as disclosed in EP0153277, e.g. an N-acyl-14-O-[(1-amino-2-methylpropan-2-yl)thioacetyl]-mutilin or 19,20-dihydromutilin, such as of formula

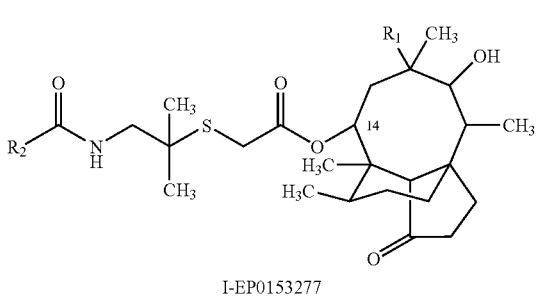

I-EP0153277 wherein $R_1$ is vinyl or ethyl positions 19 and 20), and $R_2$ is optionally hydroxy-substituted aminoalkyl or a 5-membered saturated heterocycle, e.g. including Valnemulin (Econor®) of formula

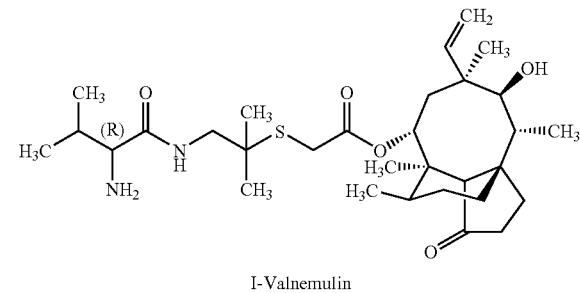

I-Valnemulin

A compound as disclosed in U.S. Pat. No. 516,526, e.g. of formula

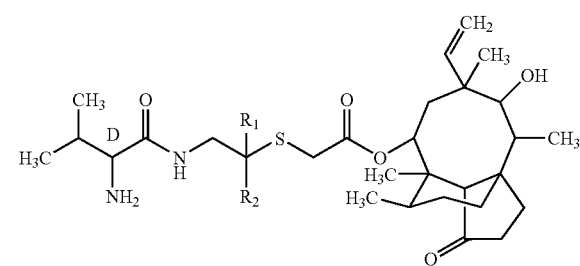

I-U.S. Pat. No. 5,164,526 wherein $R_1$ and $R_2$ independently of each other are H, alkyl, alkenyl, cycloalkyl, aryl or aralkyl;

A compound as disclosed in WO9322288, e.g. of formula

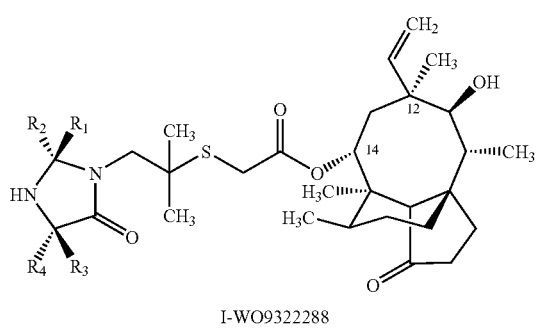

I-WO9322288 wherein $R_1$ and $R_2$ are independently of each other H, alkyl, or, $R_1$ and $R_2$ together with the carbon atom to which they are attached are cycloalkyl; and $R_3$ and $R_4$ independently of each other are H, alkyl or substituted alkyl;

A compound as disclosed in WO9725309, e.g. of formula

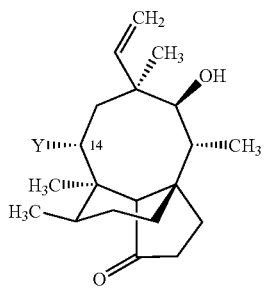

I-WO9725309 wherein Y is carbamoyloxy, wherein the N-atom is unsubstituted or mono- or disubstituted, such as a compound of formula

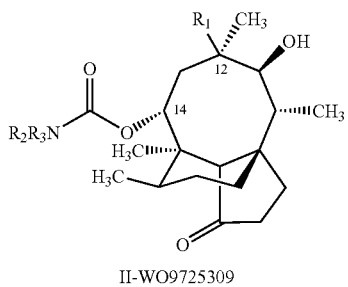

II-WO9725309 wherein $R_1$ is vinyl or ethyl, $R_2$ and $R_3$ independently of each other are H, or optionally substituted
saturated or unsaturated ($C_{1-6}$)hydrocarbon or ($C_{3-8}$)cyclic hydrocarbon,
heterocyclyl or aryl, or
$R_2$ and $R_3$ together form an optionally substituted cyclic group of 3 to 8 ring atoms, optionally containing one additional heteroatom selected from N, O and S, and optionally fused to a hydrocarbon ring, a heterocyclic group or an aromatic group; or
$R_2$ is one of the above monovalent groups and $R_3$ is a group selected form $SO_2R_4$, $COR_5$,
$OR_5$ and $NR_6R_7$; wherein
$R_4$ is optionally substituted,
saturated or unsaturated ($C_{1-6}$)hydrocarbon or ($C_{3-8}$)cyclic hydrocarbon,
heterocyclyl, aryl, ($C_{1-6}$)alkylamino or arylamino;
$R_5$ is optionally substituted
saturated or unsaturated ($C_{1-6}$)hydrocarbon or ($C_{3-8}$)cyclic hydrocarbon,
heterocyclyl or aryl,
$R_6$ and $R_7$ independently of each other are H, or optionally substituted
saturated or unsaturated ($C_{1-6}$)hydrocarbon or ($C_{3-8}$)cyclic hydrocarbon,
heterocyclyl or aryl, or
$R_6$ and $R_7$ together with the nitrogen atom to which they are attached form an optionally substituted ($C_{3-8}$)cyclic group, optionally containing one additional heteroatom selected from N, O or S, and optionally fused to a hydrocarbon ring, a heterocyclic ring or an aromatic group;

A compound as disclosed in WO9805659, e.g. of formula

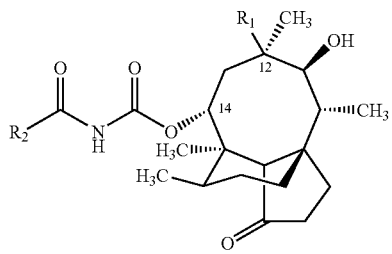

I-WO9805659 wherein $R_1$ is vinyl or ethyl, and $R_2$ is a group $R_3$, $R_4CH_2$—, or $R_5R_6CH$=CH—, wherein, each of $R_3$ and $R_4$ is an azabicyclic ring system, or $R_5$ and $R_6$ together with the carbon atom to which they are attached form an azabicyclic ring system;

A compound of WO9821855; e.g. of formula

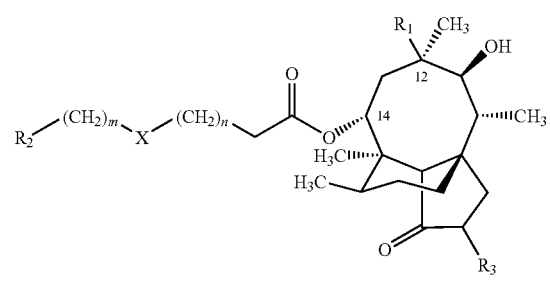

IA-WO9821855

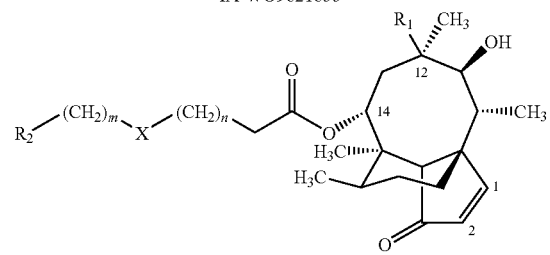

IB-WO9821855 wherein n and m are independently of each other 0, 1 or 2; X is O, S, S(O), $SO_2$, —COO—, —NH—, —CONH—, —NHCONH—, or a bond; $R_1$ is vinyl or ethyl; $R_2$ is a non-aromatic monocyclic or bicyclic group containing one or two basic nitrogen atoms and attached through a ring carbon atom, e.g. $R_2$ is optionally substituted quinuclidinyl, azabicyclo[2.2.1]heptyl, azabicyclo[4.3.0]nonyl, azabicyclo[3.2.1]octyl, azabicyclo[3.3.0]octyl, azabicyclo[2.2.2]octyl, azabicyclo[3.2.1]octenyl, azabicyclo[3.3.1]nonyl or azabicyclo[4.4.0]decyl; $R_3$ is H, OH; or the moietity $R_2(CH_2)_mX(CH_2)_nCH_2COO$ at position 14 of IA or IB is replaced by $R_aR_bC$=CHCOO, wherein one of $R_a$ or $R_b$ is hydrogen and the other is $R_2$; or $R_a$ and $R_b$ together form $R_2$;

A compound as disclosed in WO0007974, e.g. a 14-acyloxy derivative of mutilin or 19,20-dihydromutilin having a 2-fluoro substituent, such as of formula

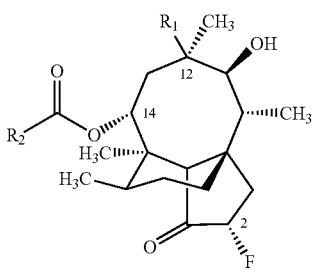

IA-WO0007974

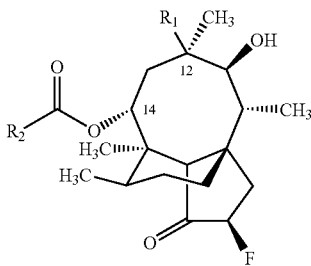

IB-WO0007974 wherein $R_1$ is vinyl or ethyl (positions 19 and 20), and $R_2COO$— is acyloxy, e.g. $HOCH_2CO_2$— or R—X—$CH_2CO_2$, wherein X is O, S or NR' and R and R' are indpendently of each other an aliphatic or aromatic group, preferably $R_2COO$— is a carbamoyl group, such as a group $R_3R_4NCO_2$— wherein $R_3$ and $R_4$ have various meanings (e.g. $R_3$ and $R_4$ have the meaning as disclosed for the meaning of $R_2$ and $R_3$ in WO9725309);

A compound as disclosed in WO0027790, e.g. a compound of formula

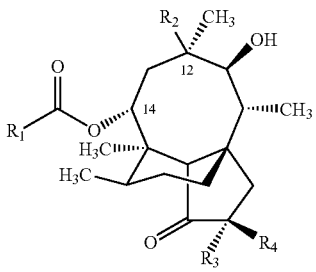

IA-WO00/27790

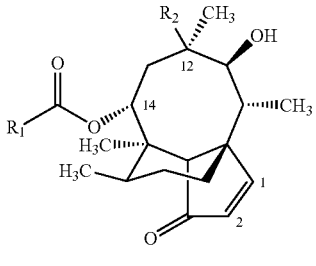

IB-WO00/27790 wherein $R_1$ is a $R^A(CH_2)_nO(CH_2)_m$, $R^A(CH_2)_p$, or a group of formula

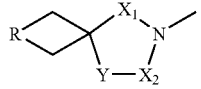

wherein R is a spiro-fused mono- or bicyclic ring containing one or two basic N-atoms; $X_1$ and $X_2$ which may be the same or different, are each —$CH_2$— or —C=O, provided that at least one of $X_1$ and $X_2$ is —C=O; and Y is —NH—, —$CH_2$— or —$CH_2$—$CH_2$—;

$R^A$ is an optionally substituted aryl group or heteroaryl group linked via a carbon atom;

e.g. $R^A$ is optionally substituted phenyl, thienyl, pyridinyl, furyl, thiazolyl, isoxazolyl, benzimidazolyl, quinolinyl, 1,2,3,4-tetrahydro-isoquinolinyl or benzthiazolyl:

m is 1, 2 or 3; n is 0, 1 or 2; p is 1 to 4; $R_2$ is vinyl or ethyl; and $R_3$ is H, OH or F, and $R_4$ is H; or $R_3$ is H and $R_4$ is F;

A compound as disclosed in WO0037074, e.g. a compound of formula

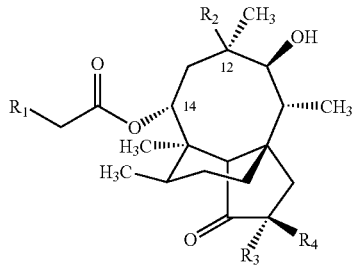

IA-WO0037074

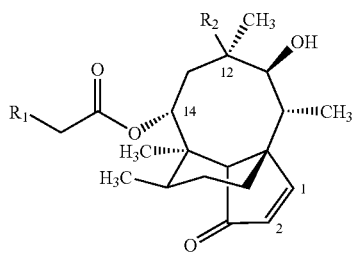

IB-WO0037074 wherein $R_1$ is an optionally substituted heteroaryl group which comprises a 5-membered heteroaromatic ring which has at least one N-atom, e.g. a pyrrole, pyrazole, imidazole, 1,2,3-triazole, 1,2,4-triazole, indole, benzimidazole, benzotriazole, 2-aza-indole or 6-aza-indole; and which is linked via a N-atom; $R_2$ is vinyl or ethyl; $R_3$ is H, OH or F, and $R_4$ is H; or $R_3$ is H and $R_4$ is F;

A compound as disclosed in WO0073287, e.g. a compound of formula

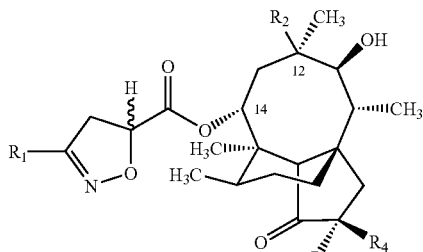

IA-WO0073287

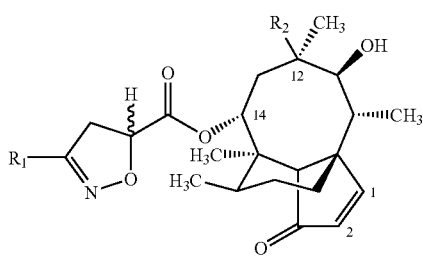

IB-WO0073287 wherein $R_1$ is optionally substituted aryl, e.g. azabicyclo-octyl; or an optionally substituted nitrogen containing ring, e.g. piperidinyl; $R_2$ is vinyl or ethyl; $R_3$ is H, OH or F and $R_4$ is H; or
$R_3$ is H and $R_4$ is F;

A compound as disclosed in WO0114310, e.g. a compound of formula

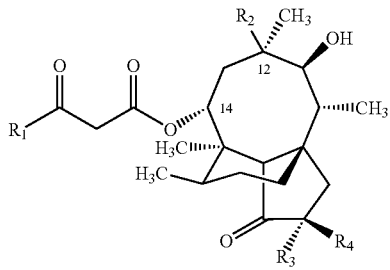

IA-WO0114310

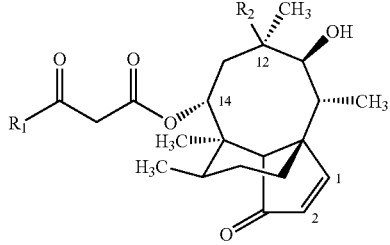

IB-WO0114310 wherein $R_1$ is a nitrogen containing heterocycle, an optionally substituted aryl or optionally subsituted heteroaryl, or $CH_2R_5$, e.g. $R_1$ is optionally substituted phenyl, 3-pyridyl, 4-pyridyl, pyrimidin-2-yl, 1,3,4-thiadiazol-2-yl, benzothiazol-2-yl. 2H-1,2,4-triazol-3-yl, azabicycloheptyl, azabicyclooctyl or piperidinyl;

$R_2$ is vinyl or ethyl; $R_3$ is H, OH or F and $R_4$ is H; or $R_3$ is H and $R_4$ is F; $R_5$ is halogen or $SR_6$; and $R_6$ is aminoalkyl, a nitrogen containing heterocycle, or an optionally substituted aryl or optionally subsituted heteroaryl; e.g. $R_6$ is optionally substituted phenyl, 3-pyridyl, 4-pyridyl, pyrimidin-2-yl, 1,3,4-thiadiazol-2-yl, benzothiazol-2-yl. 2H-1,2,4-triazol-3-yl, azabicycloheptyl, azabicyclooctyl or piperidinyl;

A compound as disclosed in WO0109095, e.g. a compound of formula

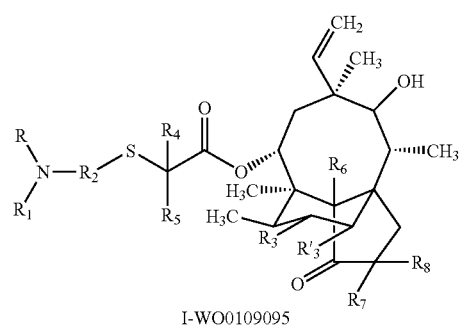

I-WO0109095 wherein R is hydrogen or alkyl; $R_1$ is hydrogen or a group of formula

wherein X is S, O, or $NR_{10}$, wherein $R_{10}$ is H or alkyl, or $N^+(R'_{10})_2$ wherein $R'_{10}$ is alkyl in the presence of an appropriate anion; and $R_9$ is amino, alkyl, aryl, heterocyclyl or mercapto; and, if X is oxygen, $R_9$ is additionally hydrogen; $R_2$ is arylene, e.g. phenylene; or heterocyclene; $R_4$ is hydrogen or alkyl; $R_5$ is hydrogen or alkyl; $R_3$, $R_3'$, $R_6$, $R_7$ and $R_8$ independently of each other are hydrogen or deuterium; or R and $R_2$ together with the nitrogen atom to which they are attached form non-aromatic heterocyclene and $R_1$ is a group of formula

wherein X and $R_9$ are as defined above; e.g. a compound of formula

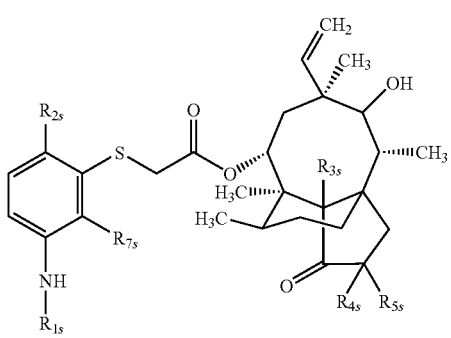

$I_s$-WO0109095 wherein $R_{1s}$ is hydrogen or a group of formula

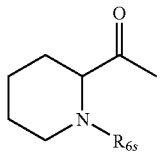

wherein $R_{6s}$ is hydrogen or deuterium; $R_{2s}$ is hydrogen, methyl or tert-butyl;

$R_{7s}$ is hydrogen or methyl; and $R_{3s}$, $R_{4s}$ and $R_{5s}$ are hydrogen or deuterium;

A compound as disclosed in WO0174788, e.g. a compound of formula

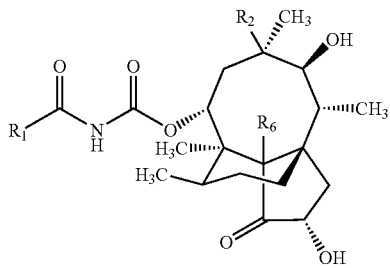

I-WO0174788 wherein $R_1$ is a 5- or 6-membered optionally substituted heteroaryl group;

e.g. pyridine, pyridazine, pyrimidine, pyrazine, isoxazole, thiazole, imidazole, pyrazole, 1,2,3-triazole, 1,2,4-triazole, benzimidazole, 3-oxo-3,4-dihydropyrido[2,3-b]pyrazine, or pyrazolo[1,5-a]pyrimidine; and $R_2$ is vinyl or ethyl;

A compound as disclosed in WO0204414, e.g. a compound selected from 14-O-[(cycloalkyl-sulfanyl)acetyl]mutilins; 14-O-[(cycloalkyl-alkyl-sulfanyl)acetyl]mutilins; 14-O-[(cycloalkoxy)acetyl]mutilins; or 14-O-[(cycloalkyl-alkoxy)acetyl]mutilins, such as of formula

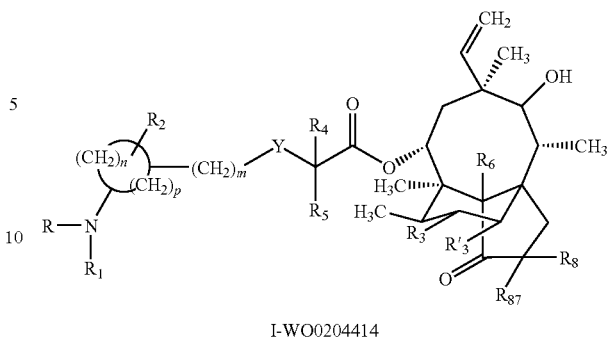

I-WO0204414 wherein R is hydrogen; $R_1$ is hydrogen or a group of formula

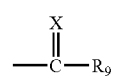

wherein X is sulphur, oxygen or $NR_{10}$, wherein $R_{10}$ is hydrogen or alkyl; and $R_9$ is amino, alkyl, aryl or heterocyclyl; and, if X is oxygen, $R_9$ is additionally hydrogen; Y is sulphur or oxygen; $R_2$ is hydrogen or one or more substituents, $R_4$ is hydrogen or alkyl; $R_5$ is hydrogen or alkyl; $R_3$ and $R_3'$ are hydrogen, deuterium, or halogen; $R_6$, $R_7$ and $R_8$ are hydrogen or deuterium; m is a number selected from 0 to 4; n is a number selected from 0 to 10; and p is a number selected from 0 to 10; with the proviso that n plus p are at least 1;

e.g. a compound of formula

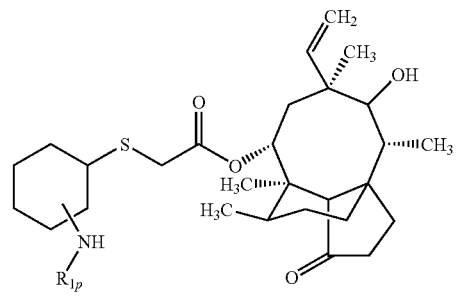

$I_p$-WO0204414 wherein $R_{1p}$ is hydrogen or the residue of an amino acid;

A compound as disclosed in WO0212199, e.g. a compound of formula

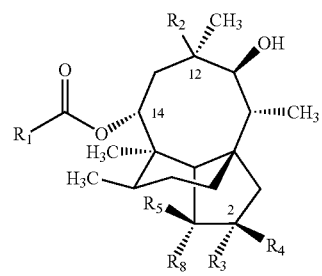

IA-WO0212199

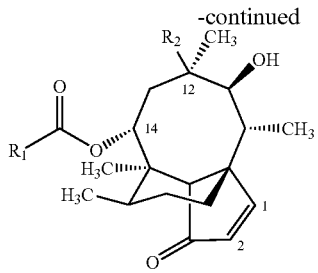

IB-WO0212199 wherein R₁ is:
a 5- or 6-membered aromatic or heteroaromatic ring attached via a ring carbon atom, preferably pyridyl, and comprising a substituent selected from halo, $R_7O-$, $R_7S-$ or $R_8R_9N-$ on a ring carbon adjacent to the carbon of attachment; or a 5- or 6-membered dihydro heteroaromatic ring attached via a ring carbon atom and comprising one oxygen or one or two nitrogen atoms and optionally fused to phenyl, a 5- or 6-membered heteroaryl ring comprising one or two nitrogen atoms or a 5- or 6-membered heterocyclyl ring comprising a sulphur, oxygen or nitrogen atom and further comprising a substituent selected from oxo or thioxo on a ring carbon adjacent to the carbon of attachment;

a 6-membered tetrahydro heteroaromatic ring attached via a ring carbon atom comprising one or two nitrogen atoms and further comprising two substituents independently selected from oxo or thioxo wherein one of the substituents is on a ring carbon adjacent to the carbon of attachment; or a bicyclic heteroyaryl ring attached via a ring carbon atom and comprising nine or ten ring atoms and from one to four nitrogen atoms;

wherein the ring of R₁ may be optionally further substituted; R₂ is vinyl or ethyl; R₃ is H, OH or F and R₄ is H, or R₃ is H and R₄ is F; and R₅ and R₆ together form an oxo group; or R₃ and R₄ is each H and R₅ is H, or OH and R₆ is H, or R₅ is H and R₆ is H or OH; R₇ is optionally substituted $(C_{1-6})$alkyl; and R₈ and R₉ are independently selected from hydrogen or optionally substituted $(C_{1-6})$alkyl.

A compound as disclosed in WO0222580, of formula

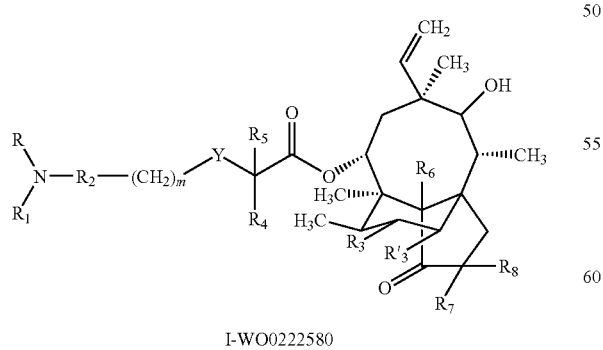

I-WO0222580 wherein R and R₂ together with the nitrogen atom to which they are attached form pyrrolidinyl or piperidinyl, R₁ is a group of formula

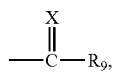

R₃ and R'₃ are hydrogen, deuterium or halogen, R₄ is hydrogen or alkyl, R₅ is hydrogen or alkyl, R₆, R₇ and R₈ are hydrogen or deuterium; R₉ is amino, alkyl, aryl, heterocyclyl or mercapto; and, if X is oxygen, R₉ is additionally hydrogen; R₁₀ is hydrogen or alkyl, R'₁₀ is alkyl, X is sulphur, oxygen, NR₁₀, or $N^+(R'_{10})_2$ in the presence of an appropriate anion, Y is sulphur or oxygen, and m is 0, 1 or 2;

with the proviso that, when R and R₂ together with the nitrogen atom to which they are attached form piperidinyl, m is 0, Y is S and Y is attached in position 3 of said piperidine ring that group of formula I which is attached to the piperidine ring via the residue Y is either in the (S)-configuration or in the (R)-configuration, preferably in the (S)-configuration; preferably a compound of formula

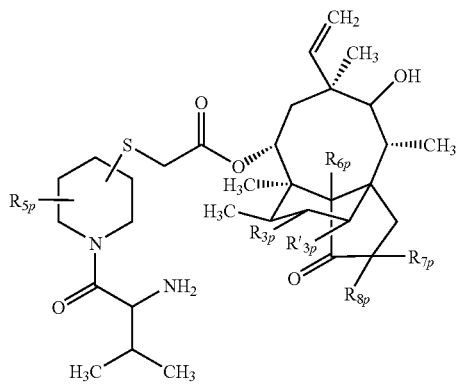

I$_p$-WO0222580 wherein R$_{3p}$, R'$_{3p}$, R$_{6p}$, R$_{7p}$ and R$_{8p}$ are, index-number correspondingly, as defined for a compound of formula I-WO0222580 for R₃, R'₃, R₆, R₇ and R₈; and R$_{5p}$ is hydrogen or one or more substituents, and if the group attached to the piperidine ring via the sulphur atom is In position 3 of said piperidine ring and R$_{5p}$ is hydrogen, then the group attached to the sulphur atom is either in the (S)-configuration or in the (R)-configuration;

a compound of formula

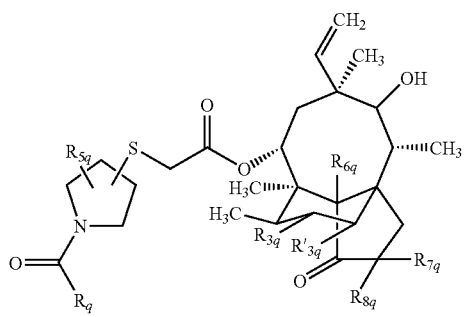

I$_q$-WO0222580 wherein $R_{3q}$, $R'_{3q}$, $R_{6q}$, $R_{7q}$ and $R_{8q}$ are, index-number correspondingly, as defined for a compound of formula $I$-WO0222580 for $R_3$, $R'_3$, $R_6$, $R_7$ and $R_8$; $R_{5q}$ is hydrogen or one or more substituents, preferably hydrogen; and $R_q$ is that part of an amino acid which remains if the carboxylic group is splitt off;

a compound of formula

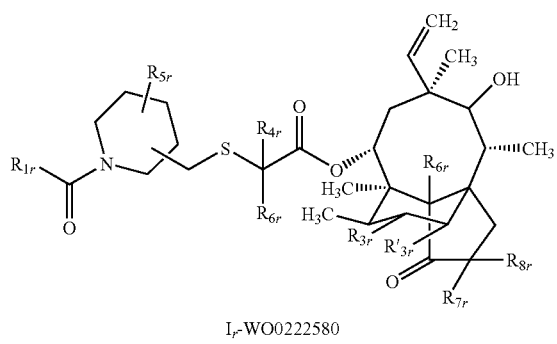

$I_r$-WO0222580 wherein $R_{3r}$, $R'_{3r}$, $R_{4r}$, $R_{6r}$, $R_{7r}$ and $R_{8r}$ are, index-number correspondingly, as defined for a compound of formula WO0222580 for $R_3$, $R'_3$, $R_4$, $R_6$, $R_7$ and $R_8$; $R_{5r}$ is hydrogen or one or more substituents, and $R_{1r}$ is that part of an amino acid which remains if the carboxylic group is splitt off, or a compound of formula

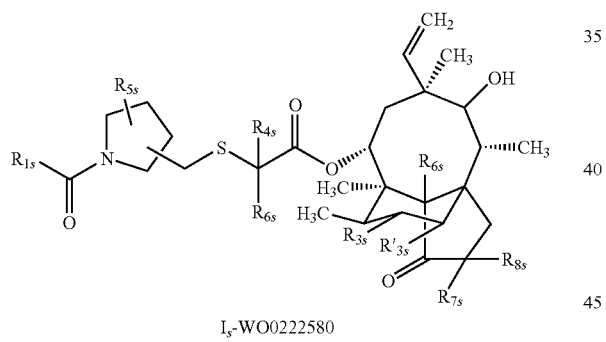

$I_s$-WO0222580 wherein $R_{3s}$, $R'_{3s}$, $R_{4s}$, $R_{6s}$, $R_{7s}$ and $R_{8s}$, respectively, are, index-number correspondingly, as defined for a compound of formula $I$-WO0222580 for $R_3$, $R'_3$, $R_4$, $R_6$, $R_7$ and $R_8$;

$R_{5s}$ is hydrogen or one or more substituents, preferably hydrogen; and $R_{1s}$ is that part of an amino acid which remains if the carboxylic group is splitt off; e.g. wherein in a compound of formula $I_s$ the group attached to the piperidine ring via the sulphur atom is either in the (S)-configuration or in the (R)-configuration; e.g. wherein in a group $R_{1s}$ the amine group of the amino acid residue is either in the (S)-configuration or in the (R)-configuration;

A compound which is selected from the group consisting of compounds of formulae

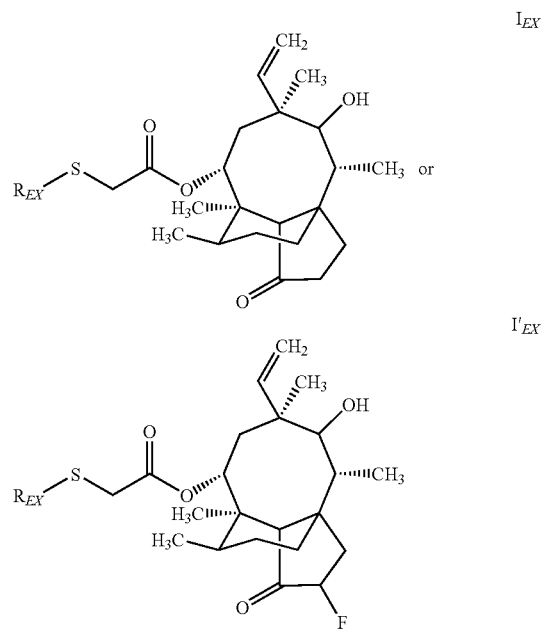

wherein $R_{EX}$ is as set out in TABLE 1 (in all Examples of TABLE 1 the compounds are of formula $I_{EX}$, with the exception of Example 12 in which the compound is of formula $I'_{EX}$; $^1$H-NMR-data of the compounds described and obtained according, e.g. analogously, to a method as described in the examples, are also indicated in TABLE 1):

TABLE 1

| $R_{EX}$ | |
|---|---|
| 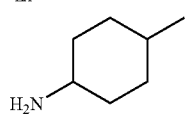 | Example 1<br>14-O-[4-Amino-cyclohexan-1-yl-sulfanyl)-acetyl]-mutilin in the form of a hydrochloride<br>($d_6$-DMSO): 7.9(b, 3H, NH$_3$), AB-system($v_A$=3.23, $v_B$=3.29, 2H, H$_{22}$, J=15.2Hz), 3.03(m, 1H, SCH), 3.10(m, 1H, CHN) |
| $R_{EX}$<br>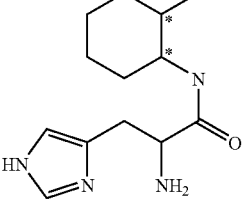 | Example 2<br>14-O-[(2-(R*)-((R)-Histidinyl)-amino-cyclohexan-1-(S*)-yl)-sulfanyl acetyl)]-mutilin in the form of a hydrochloride<br>($d_6$-DMSO): Diastereoisomers: 8.4, 9.0(2xm, 2H, NH), 7.5, 8.7 (2xb, 2H, imidazole), 6.15, 5.1(2xm, H$_{19}$, H$_{20}$, H$_{21}$), 5.52(d, 1H, J=5.2Hz, H$_{14}$), 4.2(m, 1H, a-H-histidine)3.45(m, 1H, H$_{11}$), 3.3(m, 2H, H$_{22}$), 2.7(m, 1H, CHS), 1.18, 1.45(2xs, (CH3)$_{15}$, (CH3)$_{18}$), 0.75, 0.88(2xd, (CH$_3$)$_{16}$, (CH$_3$)$_{17}$, J=5.4Hz) |

TABLE 1-continued

| $R_{EX}$ | |
|---|---|
| 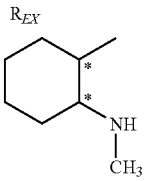 | Example 3a<br>14-O-[(2-(R*)-Methylamino-cyclohexan-1-(S*)-yl)-sulfanyl acetyl)]-mutilin<br>($d_6$-DMSO): Diastereoisomers: 6.15, 5.1(2xm, $H_{19}$, $H_{20}$, $H_{21}$), 5.52(d, 1H, J=5.2Hz, $H_{14}$), 4.50(d, 1H, OH, J=5Hz), 3.45(t, 1H, $H_{11}$, J=5Hz), 3.25(m, 2H, $H_{22}$), 3.25(m, 1H, CHN), 2.82(m, 1H, CHS), 2.38(d, 3H, $CH_3$NH, J=5.1Hz), 1.3, 1.34)1.18, 1.45(2xs, $(CH3)_{15}$, $(CH3)_{18}$), 0.75, 0.88(2xd, $(CH_3)_{16}$, $(CH_3)_{17}$, J=5.4Hz). |
| 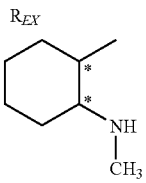 | Example 3b<br>14-O-[(2-(R*)-Methylamino-cyclohexan-1-(R*)-yl)-sulfanyl acetyl)]-mutilin<br>($d_6$-DMSO): Diastereoisomers: 6.15, 5.1(2xm, $H_{19}$, $H_{20}$, $H_{21}$), 5.52(d, 1H, J=5.2Hz, $H_{14}$), 4.50(d, 1H, OH, J=5Hz), 3.45(t, 1H, $H_{11}$, J=5Hz), 3.25(m, 2H, $H_{22}$), 3.25(m, 1H, CHN), 2.65(m, 1H, CHS), 2.43(d, 3H, $CH_3$NH, J=5.1Hz), 1.3, 1.34)1.18, 1.45(2xs, $(CH3)_{15}$, $(CH3)_{18}$), 0.75, 0.88(2xd, $(CH_3)_{16}$, $(CH_3)_{17}$, J=5.4Hz) |
| 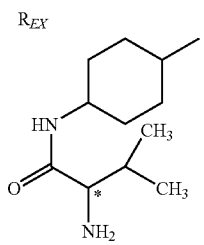 | Example 4<br>(14-O-[4-((R)-Valyl-amino-cyclohexane-1-yl)-sulfanyl)-acetyl]-mutilin in the form of a hydrochloride<br>($CD_3OD$): 8.3(d, 1H, NH), 8.1(b, 3H, $NH_3$), 6.15(m, 1H, H19), 5.55(d, 1H, H14), 5.05(m, 2H, H20), 3.75(m, 1H, NCHCO), 3.3(m, 1H, NCH), 3.42(d, 1H, H11), 3.25(m, 2H, $SCH_2CO$), 2.98(m, 1HCHS), 0.9(d, 6H, $(CH_3)_2CH$), 1.08, 1.36(2xs, 6H, $(CH_3)_{18}$, $(CH_3)_{15}$), 0.65, 0.83(2xd, 6H, $(CH_3)_{16}$, $(CH_3)_{17}$) |
| 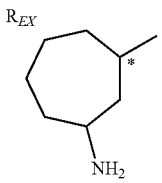 | Example 5a<br>14-O-[((3-(R*)-Amino-cycloheptan-1(R*)-yl)sulfanyl)acetyl]-mutilin and 14-O-[((3-(S*)-amino-cycloheptan-1(S*)-yl)-sulfanyl)-acetyl]mutilin in the form of a hydrochloride (diastereoisomeric mixture)<br>($d_6$-DMSO): 8.0(b, 3H, $NH_3^+$), 6.15, 5.1(2xm, $H_{19}$, $H_{20}$, $H_{21}$), 5.52(d, 1H, J=5.2Hz, $H_{14}$), 3.1, 3.2(2xm1H, $CHNH_3^+$), 3.4(m, 1H, $H_{11}$,), 3.3(m, 2H, $H_{22}$), 2.9(m, 1H, SCH), 1.18, 1.45(2xs, $(CH3)_{15}$, $(CH3)_{18}$), 0.9(m, 6H, $CH(CH_3)_2$), 0.75, 0.88(2xd, $(CH_3)_{16}$, $(CH_3)_{17}$, J=5.4Hz)<br>Example 5b<br>14-O-[((3-(R*)-Amino-cycloheptan-1(S*)-yl)sulfanyl)acetyl]-mutilin and 14-O-[((3-(S*)-Amino-cycloheptan-1(R*)-yl)sulfanyl)acetyl]-mutilin in the form of a hydrochloride (diastereoisomeric mixture)<br>($d_6$-DMSO): 7.8(b, 3H, $NH_3^+$), 6.15, 5.1(2xm, $H_{19}$, $H_{20}$, $H_{21}$), 5.52(d, 1H, J=5.2Hz, $H_{14}$), 3.15(2xm1H, $CHNH_3^+$), 3.4(m, 1H, $H_{11}$,), 3.3(m, 2H, $H_{22}$), 2.95(m, 1H, SCH), 1.18, 1.45(2xs, $(CH3)_{15}$, $(CH3)_{18}$), 0.9(m, 6H, $CH(CH_3)_2$), 0.75, 0.88(2xd, $(CH_3)_{16}$, $(CH_3)_{17}$, J=5.4Hz) |
| 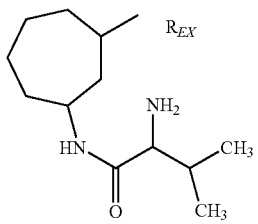 | Example 6<br>14-O-[(3-(R/S)-(R)-Valylamino-1-(R/S)-yl)sulfanyl)acetyl]mutilin in the form of a hydrochloride<br>($d_6$-DMSO): 8.4(m, 1H, NHC=O), 8.1(b, 3H, $NH_3^+$), 6.15, 5.1(2xm, $H_{19}$, $H_{20}$, $H_{21}$), 5.52(d, 1H, J=5.2Hz, $H_{14}$), 3.5, 3.9(2xm, 1H, a-H-valyl), 3.15(2xm1H, $CHNH_3^+$), 3.4(m, 1H, $H_{11}$,)$_2$ 3.3(m, 2H, $H_{22}$), 2.95(m, 1H, SCH), 1.18, 1.45(2xs, $(CH3)_{15}$, $(CH3)_{18}$), 0.9(m, 6H, $CH(CH_3)_2$), 0.75, 0.88(2xd, $(CH_3)_{16}$, $(CH_3)_{17}$, J=5.4Hz) |
| 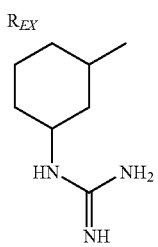 | Example 7<br>14-O-[(3-(R/S)-Guanidino-cyclohexan-1-(R/S)-yl)-acetyl]mutilin in the form of a hydrochloride<br>($d_6$-DMSO): 6.8-7.4(b, 3H, $NH_3^+$), 7.65, 7.7(2xm, 1H, NH), 6.15, 5.1(2xm, $H_{19}$, $H_{20}$, $H_{21}$), 5.52(d, 1H, J=5.2Hz, $H_{14}$), 4.5(d, 1H, OH, J=6Hz), 3.1(m1H, CHNH), 3.4(t, 1H, $H_{11}$, J=6Hz), 3.3(m, 2H, $H_{22}$), 2.7(m, 1H, SCH), 1.18, 1.45(2xs, $(CH3)_{15}$, $(CH3)_{18}$), 0.75, 0.88(2xd, $(CH_3)_{16}$, $(CH_3)_{17}$, J=5.4Hz) |

TABLE 1-continued

| $R_{EX}$ | |
|---|---|
| 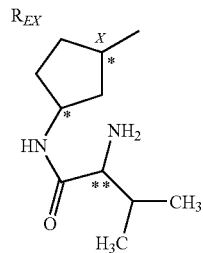 | Example 8a<br>14-O-[3-(R*)-((R)-Valyl-amino-cyclopentan-1-(S*)-yl)-sulfanyl)-ace-tyl]-mutilin in the form of a hydrochloride<br>(DMSO-d$_6$): 8.5(d, 1H, NH, J=7.2Hz), 8.1(bs, 3H, NH$_3^+$), 6.15, 5.06, 5.02(3xm, H$_{19}$, H$_{20}$, H$_{21}$), 5.55(d, 1H, H$_{14}$, J=8.2Hz), 4.05(m, 1H, H-alpha-valyl), 3.15(m, 1H, H-1'), 3.2-3.5(m, H-3', H$_{11}$, H$_{22}$), 1.35, 1.05(2xs, (CH$_3$)$_{15}$, (CH$_3$)$_{18}$), 0.91, 0.88(d, (CH$_3$)$_2$CH, J=6.8Hz), 0.8, 0.62(2xd, (CH$_3$)$_{16}$, (CH$_3$)$_{17}$, J=6.8Hz)<br>Example 8b<br>14-O-[3-(S*)-((R)-Valyl-amino-cyclopentan-1-(R*)-yl)-sulfanyl)-ace-tyl]-mutilin in the form of a hydrochloride<br>(DMSO-d$_6$): 8.5(d, 1H, NH, J=7.2Hz), 8.1(bs, 3H, NH$_3^+$), 6.15, 5.06, 5.02(3xm, H$_{19}$, H$_{20}$, H$_{21}$), 5.55(d, 1H, H$_{14}$, J=8.2Hz), 4.05(m, 1H, H☐-valyl), 3.15(m, 1H, H-1'), 3.2-3.5(m, H3', H$_{11}$, H$_{22}$), 1.35, 1.05(2xs, (CH$_3$)$_{15}$, (CH$_3$)$_{18}$), 0.91, 0.89(d, (CH$_3$)$_2$CH, J=6.9Hz), 0.8, 0.62(2xd, (CH$_3$)$_{16}$, (CH$_3$)$_{17}$, J=6.8Hz).<br>Example 8c<br>14-O-[3-(S*)-((R)-Valyl-amino-cyclopentan-1-(S*)-yl)-sulfanyl)-ace-tyl]-mutilin and 14-O-[3-(R*)-((R)-valyl-amino-cyclopentan-1-(R*)-yl)-sulfanyl-acetyl]-mutillin in the form of a hydrochloride(mixture of trans-diastereoisomers)<br>(DMSO-d$_6$): 8.52, 8.53(2xd, 1H, NH, J=6.9Hz), 8.1(bs, 3H, NH$_3^+$), 6.15, 6.12, 5.0-5.1(6xm, H$_{19}$, H$_{20}$, H$_{21}$), 5.54, 5.55(2xd, 1H, H$_{14}$, J=8.2Hz), 4.15(m, 1H, H☐-valyl), 3.1-3.5(m, H-1', H3', H$_{11}$, H$_{22}$), 1.35, 1.05(2xs, (CH$_3$)$_{15}$, (CH$_3$)$_{18}$), 0.91, 0.88(d, (CH$_3$)$_2$CH, J=6.8Hz), 0.8, 0.62(2xd, (CH$_3$)$_{16}$(CH$_3$)$_{17}$, J=6.8Hz) |
| 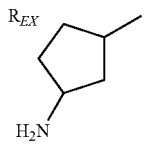 | Example 9<br>14-O-[((3-(R/S)-Amino-cyclopentyl)-sulfanyl)-acetyl]-mutilin-hydro-chloride<br>(DMSO-d$_6$): 8.03(bs, 3H, NH$_3^+$), 6.13, 5.05(2xm, 3H, H$_{19}$, H$_{20}$, H$_{21}$), 5.55(d, 1H, H$_{14}$, J=8.0Hz), 3.2-3.6(m, H-3', H$_{11}$, H$_{22}$), 3.14(m, 1H, H-1'), 1.35, 1.05(2xs, (CH$_3$)$_{15}$, (CH$_3$)$_{18}$), 0.8, 0.62(2xd, (CH$_3$)$_{16}$, (CH$_3$)$_{17}$, J=6.8Hz) |
| 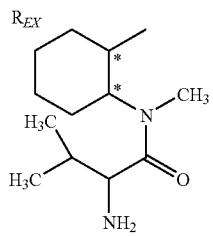 | Example 10<br>14-O-[(2-(R*)-((R)-Valyl-methylamino-cyclohexan-1-(R*)-yl)-sul-fanyl acetyl)]-mutilin in the form of a hydrochloride<br>(d$_6$-DMSO): Diastereoisomers: 8.0(m, 3H.NH$_3^+$), 6.15, 5.1(2xm, H$_{19}$, H$_{20}$, H$_{21}$), 5.52(d, 1H, J=5.2Hz, H$_{14}$), 4.50(m, 1H, OH), 4.2(m, 1H, a-H-val-ine), 3.45(m, 1H, H$_{11}$), 3.25(m, 2H, H$_{22}$), 3.25(m, 1H, CHN), 2.82(m, 1H, CHS), 2.88, 2.94(2xs, 3H, CH$_3$N), 1.3, 1.34), 1.18, 1.45(2xs, (CH3)$_{15}$, (CH3)$_{18}$), 0.75, 0.88, (2xd, (CH$_3$)$_{16}$, (CH$_3$)$_{17}$, J=5.4Hz) |
| 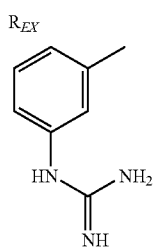 | Example 11<br>14-O-[(3-Guanidino-phenylsulfonyl)-acetyl]mutilin in the form of a hydrochloride<br>(CDCl$_3$): 0.58(d, 3H, H$_{16}$, J=7.2Hz), 0.81(d, 3H, H$_{17}$, J=7.3Hz), 1.02(s, 3H, H$_{18}$), 1.32(s, 3H, H$_{15}$), ABX-system($v_A$=1.2, $v_B$=1.88, H$_{13a}$, H$_{13b}$, J=16.1Hz, J=9.1Hz), 2.08(d, 1H, H$_4$, J=2.1Hz), ABXY-sys-tem($v_A$=2.23, $v_B$=2.19, H$_{2a}$, H$_{2b}$, J=16.2Hz, J=9.1Hz, J=1.8Hz), 2.3(m, 1H, H$_{10}$), 3.4(d, 1H, H$_{11}$, J=5.98Hz), AB-system($v_A$=3.81, $v_B$=3.89, 2H, H$_{22}$, J=14.1Hz), 5.18(dd, 1H, H$_{20a}$, J=17.5Hz, J=1.6Hz), 5.29(dd, 1H, H$_{20b}$, J=11Hz, J=1.6Hz), 5.51(d, 1H, H$_{14}$, J=8.3Hz), 6.05(dd, 1H, H$_{19}$, J=11Hz, J=17.5Hz), 7.0(m, 1H, arom.H), 7.18(m2H, arom.H), 7.3t, 1H, arom, H$_5$, J=8Hz) |
| 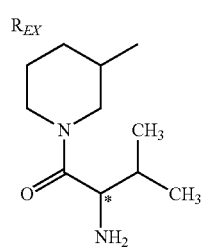 | Example 12<br>14-O-[(N-(3-Methyl-2(R)-amino-butyryl)-piperidine-3(S)-yl)-sulfanyl-acetyl]-2(S)-fluoro-mutilin in the form of a<br>hydrochloride<br>(DMSO-d$_6$): Rotamers: 7.95(bs, 3H, NH$_3^+$), 6.12, 5.05(2xm, H$_{19}$, H$_{20}$, H$_{21}$), 5.56, 5.52(2xd, 1H, H$_{14}$, J=8.3Hz), 4.92(ddd, 1H, H$_2$, J=51.3, 8.4, 8.0Hz), 4.7, 4.69(2xd, 1H, 11-OH, J=6.1Hz), 4.06(m, 1H, H☐-valyl), 4.3, 4.25, 3.91, 3.88, 2.6-3.6(m, 4xCH$_2$N, SCH, H$_{11}$, H$_{22}$), 1.39, 1.06(2xs, (CH$_3$)$_{15}$, (CH$_3$)$_{18}$), 0.99, 0.9, 0.84, 0.64(4xd, (CH$_3$)$_2$CH, (CH$_3$)$_{16}$, (CH$_3$)$_{17}$, J=6.8Hz) |

TABLE 1-continued

| $R_{EX}$ | |
|---|---|
| (piperidine with ethyl substituent, HN) | Example 13<br>14-O-[((Piperidin-3(S)-yl)methyl-sulfanyl)-acetyl]-mutilin in the form of a hydrochloride<br>($d_6$-DMSO, 350K): 6.15, 5.05(2xm, $H_{19}$, $H_{20}$, $H_{21}$), 5.55(d, 1H, 5.2Hz, $H_{14}$), 3.4(d, 1H, $H_{11}$, J=5.2Hz), 3.05, 2.95, 2.52, 2.31, 2.09, (5xm, 4H, $CH_2NCH_2$), 3.2(m, 2H, $SCH_2C=O$), 2.48(m, 2H, $CHCH_2S$), 1.18, 1.45(2xs, $(CH3)_{15}$, $(CH3)_{18}$), 0.75, 0.88, (2xd, $(CH3)_{16}$, $(CH3)_{17}$, J=5.4Hz) |
| (azepane with methyl, NH) | Example 14<br>14-O-[((Azepan-4-(R/S)-yl)-sulfanyl acetyl)]-mutilin in the form of a hydrochloride<br>400mg of 14-O-[((N-BOC-azepan-4-(R/S)-yl)-sulfanyl acetyl)-mutilin($d_6$-DMSO): 8.2-8.5(b, 2H, $NH_2^+$), 6.15, 5.1(2xm, $H_{19}$, $H_{20}$, $H_{21}$), 5.52(d, 1H, J=5.2Hz, $H_{14}$), 4.52(d, 1H, OH, J=6.2Hz)3.4(t, 1H, $H_{11}$, J=6.2Hz), 3.3(m, 2H, $H_{22}$), 2.9-3.2(2xm, 3H, SCH, CHNCH), 1.18, 1.45(2xs, $(CH3)_{15}$, $(CH3)_{18}$), 0.75, 0.88(2xd, $(CH3)_{16}$, $(CH3)_{17}$, J=5.4Hz |
| (azepane with valyl, $CH_3$, (R), $CH_3$, $NH_2$) | Example 15<br>14-O-[((N-(R)-Valyl-azepan-4-(R/S)-yl)-sulfanyl acetyl)]-mutilin-hydrochloride<br>($d_6$-DMSO): 7.7-8.0(b, 3H, $NH_3^+$), 6.15, 5.1(2xm, $H_{19}$, $H_{20}$, $H_{21}$), 5.52(d, 1H, J=5.2Hz, $H_{14}$), 4.52(d, 1H, OH, J=6.2Hz), 3.4(t, 1H, $H_{11}$, J=6.2Hz), 4.1(m, α-H-valine), 3.4, 2.6(2xm, 4H, $CH_2NCH_2$)3.3(m, 2H, $H_{22}$), 2.9 (m, 1H, SCH), 1.18, 1.45(2xs, $(CH_3)_{15}$, $(CH_3)_{18}$), 0.75, 0.88(2xd, $(CH_3)_{16}$, $(CH_3)_{17}$, J=5.4Hz) |
| (pyrrolidine with valyl) | Example 16<br>14-O-[(N-(R)-Valyl-pyrrolidin-3(s)-yl)-sulfanyl-acetyl)-mutilin-hydrochloride<br>($CD_3OD$): Rotamer, 8.1(b, 3H, NH3), 6.3-6.4(m, 1H, H19), 5.75(d, 1H, H14), 5.15(m, 2H, H20), 4.15(m, 1H, NCHCO), 3.9(m, 1H, NCH), 3.6(m, 1H, NCH), 3.42(d, 1H, H11), 3.28-3.35(m, 2H, $SCH_2CO$), 0.95, 0.98(2xd, 6H, $(CH_3)_2CH$), 1.08, 1.36(2xs, 6H, $(CH_3)_{18}$, $(CH_3)_{15}$), 0.65, 0.83(2xd, 6H, $(CH_3)_{16}$, $(CH_3)_{17}$) |
| (piperidine-pipecolyl-piperidine) | Example 17<br>14-O-[((N-(R)-Pipecolyl-piperidin-4-yl)methyl-sulfanyl)-acetyl]-mutilin in the form of a hydrochloride<br>$^1$H-NMR($d_6$-DMSO, 350K): 6.15, 5.05(2xm, $H_{19}$, $H_{20}$, $H_{21}$), 5.55(d, 1H, 5.2Hz, $H_{14}$), 3.35(d, 1H, $H_{11}$, J=5.2Hz), 4.3(m, α-H-pipecol), 4.2, 4.05, 3.75(4xm, $CH_2NCH_2$), AB-system: 3.12, 3.18, J=14.7Hz, $H_{22}$),), 2.8(m, 1H, SCH), 1.18, 1.45(2xs, $(CH3)_{15}$, $(CH3)_{18}$), 0.75, 0.88(2xd, $(CH3)_{16}$, $(CH3)_{17}$, J=5.4Hz) |

A compound of formula

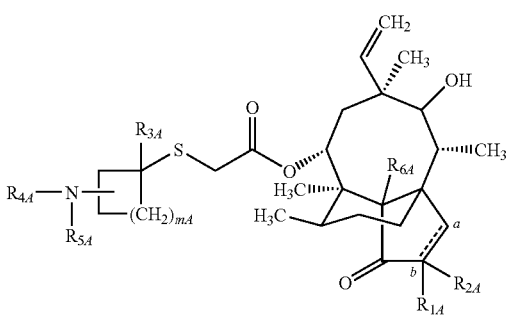

IA wherein
the dotted line is a bond (double bond between positions a=b), $R_{1A}$ is hydrogen and $R_{2A}$ is not present, or
the dotted line is no bond (single bond between positions a-b). and $R_{1A}$ and $R_{2A}$ independently of each other are hydrogen, halogen or deuterium, $R_{3A}$ is $(C_{1-6})$alkyl, $R_{4A}$ is hydrogen, $(C_{1-6})$alkyl, a group —C(=NH)—$NH_2$, or the residue of an amino acid, $R_{5A}$ is hydrogen, or $R_{4A}$ and $R_{5A}$ together are a group =CH—$NH_2$, $R_{6A}$ is hydrogen or deuterium, and $m_A$ is 0, 1, 2, 3, 4, or 5;

e.g. preferably the dotted line is no bond; $R_{1A}$ is hydrogen, $R_{2A}$ is hydrogen, $R_{3A}$ is $(C_{1-4})$alkyl, such as methyl, $R_{4A}$ and $R_{5A}$ are as defined above, $R_{6A}$ is hydrogen, and $m_A$ is 2, 3 or 4;

e.g. including pleuromutilins, which are selected from the group consisting of compounds of formula $I_X$, wherein $R_{EX}$ is as set out in TABLE 2 ($^1$H-NMR-data of the compounds described and obtained according, e.g. analogously, to a process as described in the examples are also indicated in TABLE 2):

TABLE 2

| Structure | Description |
|---|---|
| (cyclopentane with R_EX, H₃C, H₂N) | Example 18 |
| (cyclopentane with R_EX, H₃C wedge, H₂N) | Example 18a<br>14-O-[(3-(R*)-Amino-1-methyl-cyclopentan-1-(R*)-yl)-sulfanyl)-acetyl]-mutilin and 14-O-[(3-(S*)-amino-1-methyl-cyclopentan-1-(S*)-yl)-sulfanyl)-acetyl]-mutilin in the form of a hydrochloride (mixture of trans-diastereoisomers)<br>(DMSO-d₆): 7.98(bs, 3H, NH₃⁺), 6.13, 5.06, 5.03(3xm, H₁₉, H₂₀, H₂₁), 5.55(d, 1H, H₁₄, J=8.2Hz), 3.56(m, 1H, H-3'), 3.3-3.3(m, H₁₁, H₂₂), 1.36, 1.30, 1.29, 1.05(4xs, 9H, CH₃CS, (CH₃)₁₅, (CH₃)₁₈), 0.8, 0.62(2xd, (CH₃)₁₆, (CH₃)₁₇, J=6.9Hz) |
| (cyclopentane with R_EX, H₃C wedge, H₂N wedge) | Example 18b<br>14-O-[(3-(R*)-Amino-1-methyl-cyclopentan-1-(S*)-yl)-sulfanyl)-acetyl]-mutilin and 14-O-[(3-(S*)-Amino-1-methyl-cyclopentan-1-(R*)-yl)-sulfanyl)-acetyl]-mutilin in the form of a hydrochloride (mixture of cis-diastereoisomers)<br>(DMSO-d₆): 8.03(bs, 3H, NH₃⁺), 6.13, 5.06, 5.03(3xm, H₁₉, H₂₀, H₂₁), 5.53(d, 1H, H₁₄, J=8.0Hz), 4.52(bs, 1H-11-OH), 3.51(m, 1H, H-3'), 3.2-3.4(m, H₁₁, H₂₂), 1.41, 1.40, 1.35, 1.05(4xs, 9H, CH₃CS (CH₃)₁₅, (CH₃)₁₈), 0.8, 0.62(2xd, (CH₃)₁₆, (CH₃)₁₇, J=6.9Hz) |
| (structure with valyl amide) | Example 19 |
| (structure with valyl amide, stereochem) | Example 19a<br>14-O-{[(1S*,3S*)-3-((R)-2-Amino-3-methyl-butyrylamino)-1-methyl-cyclopentylsulfanyl]-acetyl}-mutilin in the form of a hydrochloride<br>Rotamer 1: (DMSO-d₆): 8.48(d, 1H, NH, J=7.1Hz), 8.1(bs, 3H, NH₃⁺), 6.11, 5.06, 5.03(3xm, H₁₉, H₂₀, H₂₁), 5.55(d, 1H, H₁₄, J=8.5Hz), 4.15(m, 1H, H□-valyl), 3.1-3.5(m, H-1', H-3', H₁₁, H₂₂), 1.35, 1.32, 1.05(3xs, CH₃CS, (CH₃)₁₅, (CH₃)₁₈), 0.91, 0.88(d, (CH₃)₂CH, J=6.8Hz), 0.8, 0.62(2xd, (CH₃)₁₆, (CH₃)₁₇, J=6.8Hz).<br>Rotamer 2: (DMSO-d₆): 8.48(d, 1H, NH, J=7.1Hz), 8.1(bs, 3H, NH₃⁺), 6.11, 5.06, 5.03(3xm, H₁₉, H₂₀, H₂₁), 5.55(d, 1H, H₁₄, J=8.5Hz), 4.5(bs, 1H, 11-OH), 4.15(m, 1H, H□-valyl), 3.1-3.5(m, H-1', H-3', H₁₁, H₂₂), 1.35, 1.32, 1.05(3xs, CH₃CS, (CH₃)₁₅, (CH₃)₁₈), 0.91, 0.88(d, (CH₃)₂CH, J=6.8Hz), 0.8, 0.62(2xd, (CH₃)₁₆, (CH₃)₁₇, J=6.8Hz) |
| (structure with valyl amide, opposite stereochem) | Example 19b<br>14-O-{[(1R*,3R*)-3-((R)-2-Amino-3-methyl-butyrylamino)-1-methyl-cyclopentylsulfanyl]-acetyl}mutilin-hydrochloride<br>(DMSO-d₆): Rotamers: 8.53(d, 1H, NH, J=7.2Hz), 8.1(bs, 3H, NH₃⁺), 6.12, 5.06, 5.03(3xm, H₁₉, H₂₀, H₂₁), 5.55(d, 1H, H₁₄, J=8.4Hz), 4.52(d, 1H, 11-OH, J=6.1Hz), 4.25(m, 1H, H□-valyl), 3.2-3.5(m, H-1', H-3', H₁₁, H₂₂), 1.42, 1.39, 1.35, 1.05(4xs, 9H, CH₃CS, (CH₃)₁₅, (CH₃)₁₈), 0.91, 0.88(d, (CH₃)₂CH, J=6.8Hz), 0.8, 0.62(2xd, (CH₃)₁₆, (CH₃)₁₇, J=6.8Hz) |

TABLE 2-continued

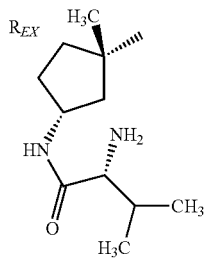

Example 19c
14-O-{[(1R*,3S*)-3-((R)-2-Amino-3-methyl-butyrylamino)-1-methyl-cyclopentylsulfanyl]-acetyl}-mutilin and
14-O-{[(1S*,3R*)-3-((R)-2-Amino-3-methyl-butyrylamino)-1-methyl-cyclopentylsulfanyl]-acetyl}-mutilin in the form of a hydrochloride(mixture of cis-diastereoisomers)
(DMSO-$d_6$): 8.4, 8.3(2xd, 1H, NH, J=7.2Hz), 8.17(bs, 3H, $NH_3^+$), 6.12, 5.06, 5.02(3xm, $H_{19}$, $H_{20}$, $H_{21}$), 5.55(d, 1H, $H_{14}$, J=8.3Hz), 4.53(bs, 1H, 11-OH), 4.15(m, 1H, H▢-valyl), 3.2-3.5(m, H-1', H-3', $H_{11}$, $H_{22}$), 1.36, 1.35, 1.32, 1.05(4xs, 9H, $CH_3CS$, $(CH_3)_{15}$, $(CH_3)_{18}$), 0.92, 0.91, 0.89, 0.88(2xd, 6H, $(CH_3)_2CH$, J=6.8Hz), 0.8, 0.62(2xd, $(CH_3)_{16}$, $(CH_3)_{17}$, J=6.8Hz)

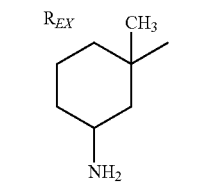

Example 20
14-O-[((3-(R/S)-Amino-cyclohexan-1-(R/S0-methyl-1-yl)sulfanyl)acetyl]mutilin in the form of a hydrochloride
($d_6$-DMSO): Rotamers: 7.90(b, 3H, $NH_3^+$), 6.15, 5.1(2xm, $H_{19}$, $H_{20}$, $H_{21}$), 5.52(d, 1H, J=5.2Hz, $H_{14}$), 4.5(2xd, 1H, OH, J=6Hz), 3.4(t, 1H, $H_{11}$, J=6Hz), 3.3(m, 2H, $H_{22}$), 3.1(m, 1H, NCH), 1.2, 1.25(2xs, 3H, $CH_3CS$)-1.18, 1.45(2xs, $(CH3)_{15}$, $(CH3)_{18}$), 0.9(m, 6H, $CH(CH_3)_2$), 0.75, 0.88(2xd, $(CH3)_{16}$, $(CH3)_{17}$, J=5.4Hz)

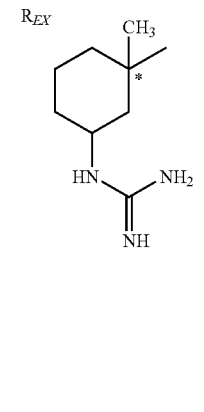

Example 21a
14-O-[(3-(R*)-Guanidino-cyclohexan-1-(R*)-methyl-1-yl)-acetyl]mutilin in the form of a hydrochloride+14-O-[(3-(S*)-Guanidino-cyclohexan-1-(S*)-methyl-1-yl)-acetyl]mutilin in the form of a hydrochloride
($d_6$-DMSO): 10.7, 8.6, 7.65, (3xm, 2H, NH), 6.7-7.5(b, 2HNH), 6.15, 5.1(2xm, $H_{19}$, $H_{20}$, $H_{21}$), 5.52(d, 1H, J=5.2Hz, $H_{14}$), 5.5(d, 1H, OH, J=6Hz), 3.9, 3.6(2x, m1H, CHNH), 3.4(t, 1H, $H_{11}$, J=6Hz), 3.3(m, 2H, $H_{22}$), 1.4, 1.45(2xs, 3H, $CH_3CS$), 1.18, 1.45(2xs, $(CH3)_{15}$, $(CH3)_{18}$), 0.75, 0.88(2xd, $(CH_3)_{16}$, $(CH3)_{17}$, J=5.4Hz).
Example 21b 14-O-[(3-(R*)-Guanidino-cyclohexan-1-(S*)-methyl-1-yl)-acetyl]mutilin in the form of a hydrochloride+
14-O-[(3-(S*)-Guanidino-cyclohexan-1-(R*)-methyl-1-yl)-acetyl]mutilin in the form of a hydrochloride
($d_6$-DMSO): 10.7, 8.6, 7.65, (3xm, 2H, NH), 6.7-7.5(b, 2HNH), 6.15, 5.1(2xm, $H_{19}$, $H_{20}$, $H_{21}$), 5.52(d, 1H, J=5.2Hz, $H_{14}$), 5.5(d, 1H, OH, J=6Hz), 3.9, 3.6(2x, m1H, CHNH), 3.4(t, 1H, $H_{11}$, J=6Hz), 3.3(m, 2H, $H_{22}$), 1.4, 1.45(2xs, 3H, $CH_3CS$), 1.18, 1.45(2xs, $(CH3)_{15}$, $(CH3)_{18}$), 0.75, 0.88(2xd, $(CH_3)_{16}$, $(CH3)_{17}$, J=5.4Hz)

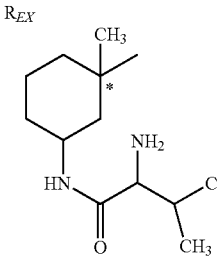

Example 22a
14-O-[(3-(R*)-(R)-Valylamino-1-(R*)-methyl-1-yl)sulfanyl)-acetyl]mutilin and 14-O-[(3-(S*)-(R)-Valylamino-1-(S*)-methyl-1-yl)sulfanyl)-acetyl]mutilin in the form of a hydrochloride
(diastereoisomeric mixture)
($d_6$-DMSO): 8.3(m, 1H, NHC=O), 8.1(b, 3H, $NH_3^+$), 6.15, 5.1(2xm, $H_{19}$, $H_{20}$, $H_{21}$), 5.52(d, 1H, J=5.2Hz, $H_{14}$), 3.9(m, 1H, a-H-valyl), 3.3-3.1(4xm, 4H, $H_{11}$, $H_{22}$, $CHNH_3^+$), 4.5(b, 1H, OH), 1.25(b, 3H, $CH_3CS$), 1.18, 1.45(2xs, $(CH3)_{15}$, $(CH3)_{18}$), 0.9(m, 6H, $CH(CH_3)_2$), 0.75, 0.88(2xd, $(CH_3)_{16}$, $(CH_3)_{17}$, J=5.4Hz)
Example 22b
14-O-[(3-(R*)-(R)-Valylamino-1-(S*)-methyl-1-yl)sulfanyl)-acetyl]mutilin and 14-O-[(3-S*)-(R)-Valylamino-1-(R*)-methyl-1-yl)sulfanyl)-acetyl]mutilin in the form of a hydrochloride
(diastereoisomeric mixture)
($d_6$-DMSO): 8.35(m, 1H, NHC=O), 8.1(b, 3H, $NH_3^+$), 6.15, 5.1(2xm, $H_{19}$, $H_{20}$, $H_{21}$), 5.52(d, 1H, J=5.2Hz, $H_{14}$), 3.95(m, 1H, a-H-valyl), 3.75(m, 1H, CHNH), 3.2-3.5(3xm, 3H, $H_{11}$, $H_{22}$,), 4.5(b, 1H, OH), 1.25(b, 3H, $CH_3CS$), 1.18, 1.45(2xs, $(CH3)_{15}$, $(CH3)_{18}$), 0.9(m, 6H, $CH(CH_3)_2$), 0.75, 0.88(2xd, $(CH_3)_{16}$, $(CH_3)_{17}$, J=5.4Hz)

Example 23
14-O-[(3-(R/S)-Dimethylamino-methylenimino-cyclohexan-1-(R/S)-methyl-1-yl)-acetyl]mutilin in the form of a hydrochloride
($d_6$-DMSO): 9.2, 8.1(2xb, 2H, NH), 6.15, 5.1(2xm, $H_{19}$, $H_{20}$, $H_{21}$), 5.52(d, 1H, J=5.2Hz, $H_{14}$), 4.5(d, 1H, OH, J=6Hz), 3.7(,m1H, CHNH), 3.4(t, 1H, $H_{11}$, J=6Hz), 3.3(m, 2H, $H_{22}$), 3.1(b, 6H, $N(CH_3)_2$), 1.4, 1.45(2xs, 3H, $CH_3CS$), 1.18, 1.45(2xs, $(CH3)_{15}$, $(CH3)_{18}$), 0.75, 0.88(2xd, $(CH_3)_{16}$, $(CH_3)_{17}$, J=5.4Hz)

14-O-(oximino-($C_{3-8}$)cycloalkyl-sulfanylmethylcarbonyl)-pleuromutilins and 14-O-(hydrazo-no-($C_{3-8}$)cycloalkyl-sulfanylmethylcarbonyl)-pleuromutilins, such as a compound of formula

IB wherein
$R_{1B}$ has the meaning of $R_{1A}$ as defined in formula $I_A$,
$R_{2B}$ has the meaning of $R_{2A}$ as defined in formula $I_A$,
$R_{10B}$ has the meaning of $R_{8A}$ as defined in formula $I_A$,
the dotted line has the meaning as defined in formula $I_A$,
$m_B$ has the meaning of ma as defined in formula $I_A$, $R_{3B}$ Is hydrogen or ($C_{1-6}$)alkyl,
$X_B$ is —O—$R_{4B}$ or —$NR_{5B}R_{6B}$,
$R_{4B}$ is hydrogen or ($C_{1-6}$)alkyl, optionally substituted by a group —$NR_{7B}R_{8B}$,
$R_{6B}$ and $R_{6B}$ independently of each other are ($C_{1-4}$)alkyl,
$R_{7B}$ and $R_{8B}$ independently of each other are ($C_{1-4}$)alkyl, or
$R_{7B}$ and $R_{8B}$ together with the nitrogen atom to which they are attached form aliphatic heterocyclyl, having 5 to 8 ring members, and
$R_{9B}$ is hydrogen or ($C_{1-4}$)alkyl;
e.g. preferably $R_{1B}$ has is hydrogen, $R_{2B}$ has is hydrogen, the dotted line is not present (single bond), $m_B$ is 2, 3 or 4, $R_{3B}$ is hydrogen or ($C_{1-4}$)alkyl, such as methyl, $X_B$ is as defined above, $R_{4B}$ is hydrogen or ($C_{1-4}$)alkyl, such as ethyl, substituted by a group —$NR_{7B}R_{8B}$, $R_{5B}$ and $R_{6B}$ are as defined above, $R_{7B}$ and $R_{8B}$ independently of each other are ($C_{1-4}$) alkyl, e.g. ethyl, or $R_{7B}$ and $R_{8B}$ together with the nitrogen atom to which they are attached form pyrrolidine or piperidine, $R_{9B}$ is as defined above, and $R_{10B}$ is hydrogen;
e.g. including 14-O-(oximino-($C_{3-8}$)cycloalkyl-sulfanylmethylcarbonyl)-pleuromutilins and 14-O-(hydrazono-($C_{3-8}$)cycloalkyl-sulfanylmethylcarbonyl)-pleuromutilins, which are selected from the group consisting of compounds of formula $I_{EX}$ wherein $R_{EX}$ is as set out in TABLE 3 ($^1$H-NMR-data of the compounds described and obtained according, e.g. analogously, to a process as described in the examples, are also indicated in TABLE 3):

TABLE 3

| $R_{EX}$ | |
|---|---|
| (cyclopentane with =N-OH and CH₃) | Example 24<br>14-O-{[(3-Hydroxyimino-cyclopentan-(R/S)-yl)-sulfanyl]-acetyl}-mutilin(syn and anti forms)<br>Syn*-form: (DMSO-$d_6$): 10.33(s, 1H, =NOH), 6.15, 5.07, 5.03(3xm, $H_{19}$, $H_{20}$, $H_{21}$), 5.55(d, 1H, $H_{14}$, J=8.3Hz), 4.5(d, 1H, 11-OH, J=6.1Hz), 3.25-3.45(m, SCH, $H_{11}$, $H_{22}$), 2.67(m, 1H, H-2a'), 1.35, 1.05(2xs, (CH$_3$)$_{15}$, (CH$_3$)$_{18}$), 0.8, 0.62(2xd, (CH$_3$)$_{16}$, (CH$_3$)$_{17}$, J=7Hz).<br>Anti*-form: (DMSO-$d_6$): 10.36(s, 1H, =NOH), 6.15, 5.07, 5.02(3xm, $H_{19}$, $H_{20}$, $H_{21}$), 5.55(d, 1H, $H_{14}$, J=8.3Hz), 4.5(d, 1H, 11-OH, J=6.1Hz), 3.25-3.45(m, SCH, $H_{11}$, $H_{22}$), 2.74(m, 1H, H-2a')1.35, 1.05(2xs, (CH$_3$)$_{15}$, (CH$_3$)$_{18}$), 0.8, 0.62(2xd, (CH$_3$)$_{16}$, (CH$_3$)$_{17}$, J=6.8Hz) |
| $R_{EX}$ (cyclopentane with CH₃, =N-OH) | Example 25a<br>14-O-{[(3-(E/Z)-Hydroxyimino-1-methyl-cyclopentan-(R*)-yl)-sulfanyl]-acetyl}-mutilin<br>$^1$HNMR(DMSO-$d_6$): 10.33, 10.28(2xs, 1H, =NOH), 6.15, 5.07, 5.02(3xm, $H_{19}$, $H_{20}$, $H_{21}$), 5.55, 5.53(2xd, 1H, $H_{14}$, J=8.3Hz), 4.5, 4.48(2xd, 1H, 11-OH, J=6.0Hz), 3.20-3.45(m, SCH, $H_{11}$, $H_{22}$), 1.35, 1.05(3xs, CH$_3$CS, (CH$_3$)$_{15}$, (CH$_3$)$_{18}$), 0.8, 0.62(2xd, (CH$_3$)$_{16}$, (CH$_3$)$_{17}$, J=6.9Hz)<br>Example 25b<br>14-O-{[(3-(E/Z)-Hydroxyimino-1-methyl-cyclopentan-(S*)-yl)-sulfanyl]-acetyl}-mutilin<br>(DMSO-$d_6$): 10.32, 10.27(2xs, 1H, =NOH), 6.15, 5.07, 5.02(3xm, $H_{19}$, $H_{20}$, $H_{21}$), 5.55(d, 1H, $H_{14}$, J=8.3Hz), 4.5(d, 1H, 11-OH, J=6.1Hz), 3.20-3.45(m, SCH, $H_{11}$, $H_{22}$), 1.35, 1.05(3xs, CH$_3$CS, (CH$_3$)$_{15}$, (CH$_3$)$_{16}$), 0.8, 0.62(2xd, (CH$_3$)$_{16}$, (CH$_3$)$_{17}$, J=6.8Hz) |
| $R_{EX}$ (cyclopentane with CH₃, =N-O-CH₂CH₂-N(C₂H₅)₂) | Example 26<br>14-O-{[(3-(2-Diethylamino-ethoxyimino)-cyclopentan-(R/S)-yl)-sulfanyl]-acetyl}-mutilin in the form of a hydrochloride<br>(syn/anti mixture)<br>(DMSO-$d_6$): 9.9(bs, 1H, NH$^+$), 6.15, 5.07, 5.03(3xm, $H_{19}$, $H_{20}$, $H_{21}$), 5.55(d, 1H, $H_{14}$, J=8.1Hz), 4.3(m, 2H, OCH$_2$), 3.1-3.4(m, NCH$_2$, $H_{11}$, $H_{22}$), 1.35, 1.05(2xs, (CH$_3$)$_{15}$, (CH$_3$)$_{18}$), 0.8, 0.62(2xd, (CH$_3$)$_{16}$, (CH$_3$)$_{17}$, J=6.8Hz) |

TABLE 3-continued

| $R_{EX}$ | |
|---|---|
| (structure: cyclohexane with HO-N= at one position and CH3 at position marked *, with ** indicating attachment) | Example 27a<br>14-O-[((E*-Hydroximino-cyclohexan-3-(R*)-yl)-sulfanyl)-acetyl]mutilin<br>(d$_6$-DMSO): 10.31(s, 1H, HON=C), 6.15, 5.1(2xm, H$_{19}$, H$_{20}$, H$_{21}$), 5.52(d, 1H, J=5.2Hz, H$_{14}$), 4.55(d, 1H, OH, J=5Hz)3.4(t, 1H, H$_{11}$, J=5Hz), 3.3(m, 2H, H$_{22}$), 2.95(m, 1H, SCH), 2.78, 1.95(2xm, 2H, CH$_2$C=N), 2.57, 2.09(2xm, 2H, CH$_2$=C=N), 1.18, 1.45(2xs, (CH3)$_{15}$, (CH3)$_{18}$), 0.75, 0.88(2xd, (CH$_3$)$_{16}$, (CH$_3$)$_{17}$, J=5.4Hz). [α]$_D$=15.87°(c=1, MeOH)<br>Example 27b<br>14-O-[((E*-Hydroximino-cyclohexan-3-(S*)-yl)-sulfanyl)-acetyl]mutilin<br>(d$_6$-DMSO): 10.31(s, 1H, HON=C), 6.15, 5.1(2xm, H$_{19}$, H$_{20}$, H$_{21}$), 5.52(d, 1H, J=5.2Hz, H$_{14}$), 4.50(d, 1H, OH, J=5Hz), 3.4(t, 1H, H$_{11}$, J=5Hz), 3.3(m, 2H, H$_{22}$), 2.95(m, 1H, SCH), 2.78, 1.95(2xm, 2H, CH$_2$C=N), 2.57, 2.09(2xm, 2H, CH$_2$=C=N), 1.18, 1.45(2xs, (CH3)$_{15}$, (CH3)$_{18}$), 0.75, 0.88(2xd, (CH$_3$)$_{16}$, (CH$_3$)$_{17}$, J=5.4Hz). [α]$_D$=38.5°(c=1, MeOH)<br>Example 27c<br>14-O-[((Z*-Hydroximino-cyclohexan-3-(R*)-yl)-sulfanyl)-acetyl]mutilin<br>(d$_6$-DMSO): 10.31(s, 1H, HON=C), 6.15, 5.1(2xm, H$_{19}$, H$_{20}$, H$_{21}$), 5.52(d, 1H, J=5.2Hz, H$_{14}$), 4.50(d, 1H, OH, J=5Hz), 3.45(t, 1H, H$_{11}$, J=5Hz), 3.3(m, 2H, H$_{22}$), 2.90(m, 1H, SCH), 3.05, 2.05(2xm, 2H, CH$_2$C=N), 2.2(m, 2H, CH$_2$=C=N), 1.18, 1.45(2xs, (CH3)$_{15}$, (CH3)$_{18}$), 0.75, 0.88(2xd, (CH$_3$)$_{16}$, (CH$_3$)$_{17}$, J=5.4Hz). [α]$_D$=13.62°(c=1, MeOH)<br>Example 27d<br>14-O-[((Z*-Hydroximino-cyclohexan-3-(S*)-yl)-sulfanyl)acetyl]mutilin<br>(d$_6$-DMSO): 10.31(s, 1H, HON=C), 6.15, 5.1(2xm, H$_{19}$, H$_{20}$, H$_{21}$), 5.52(d, 1H, J=5.2Hz, H$_{14}$), 4.50(d, 1H, OH, J=5Hz), 3.45(t, 1H, H$_{11}$, J=5Hz), 3.3(m, 2H, H$_{22}$), 2.90(m, 1H, SCH), 3.05, 2.05(2xm, 2H, CH$_2$C=N), 2.2(m, 2H, CH$_2$=C=N), 1.18, 1.45(2xs, (CH3)$_{15}$, (CH3)$_{18}$), 0.75, 0.88(2xd, (CH$_3$)$_{16}$, (CH$_3$)$_{17}$, J=5.4Hz). [α]$_D$=42.83°(c=1, MeOH) |
| (structure: cyclohexane with CH3 and * at one carbon, =N-OH group, ** attachment) | Example 28a<br>14-O-[((E-Hydroximino-cyclohexan-3-(R/S)-methyl-1-yl)-sulfanyl)acetyl]mutilin<br>(d$_6$-DMSO): 10.31(s, 1H, HON=C), 6.15, 5.1(2xm, H$_{19}$, H$_{20}$, H$_{21}$), 5.52(d, 1H, J=5.2Hz, H$_{14}$), 4.50(d, 1H, OH, J=5Hz), 3.45(t, 1H, H$_{11}$, J=5Hz), 3.25(m, 2H, H$_{22}$), 1.25(s, 3H, CH$_3$, CH$_3$CS)1.18, 1.45(2xs, (CH3)$_{15}$, (CH3)$_{18}$), 0.75, 0.88(2xd, (CH$_3$)$_{16}$, (CH$_3$)$_{17}$, J=5.4Hz)<br>Example 28b<br>14-O-[((Z-Hydroximino-cyclohexan-3-(R/S)-methyl-1-yl)-sulfanyl)acetyl]mutilin<br>(d$_6$-DMSO): 10.31(s, 1H, HON=C), 6.15, 5.1(2xm, H$_{19}$, H$_{20}$, H$_{21}$), 5.52(d, 1H, J=5.2Hz, H$_{14}$), 4.50(d, 1H, OH, J=5Hz), 3.45(t, 1H, H$_{11}$, J=5Hz), 3.25(m, 2H, H$_{22}$), 2.7(d, 1H, CHC=N, J=12Hz), 1.25(s, 3H, CH$_3$, CH$_3$CS)1.18, 1.45(2xs, (CH3)$_{15}$, (CH3)$_{18}$), 0.75, 0.88(2xd, (CH$_3$)$_{16}$, (CH$_3$)$_{17}$, J=5.4Hz) |
| (structure: cyclohexane with H$_3$C, CH$_3$ substituents and =N-OH) | Example 29<br>14-O-[((Z/E-Hydroximino-cyclohexan-3-(R/S)-methyl-5-(R/S)-methyl-1-yl)-sulfanyl)acetyl]mutilin<br>(d$_6$-DMSO): Diastereoisomers: 10.2, 10.28(3xs, 1H, HON=C), 6.15, 5.1(2xm, H$_{19}$, H$_{20}$, H$_{21}$), 5.52(d, 1H, J=5.2Hz, H$_{14}$), 4.50(d, 1H, OH, J=5Hz), 3.45(t, 1H, H$_{11}$, J=5Hz), 3.25(m, 2H, H$_{22}$), 3.25, 1.7(2xm, 2H, CH$_2$C=N), 1.3, 1.34(2xs, 3H, CH$_3$, CH$_3$CS), 1.18, 1.45(2xs, (CH3)$_{15}$, (CH3)$_{18}$), 0.75, 0.88(2xd, (CH$_3$)$_{16}$, (CH$_3$)$_{17}$, J=5.4Hz).<br>MS-ESI: 534(M+1) |
| (structure: cyclohexane with methyl, =N-O-CH$_2$CH$_2$-N(C$_2$H$_5$)$_2$) | Example 30<br>14-O-{[(3-(2-Diethylamino-ethoxyimino)-cyclohexan-(R/S)-yl)-sulfanyl]-acetyl}-mutilin hydrochloride(E/Z mixture)<br>(DMSO-d$_6$): 9.7(bs, 1H, NH$^+$), 6.15, 5.07, 5.03(3xm, H$_{19}$, H$_{20}$, H$_{21}$), 5.55(d, 1H, H$_{14}$, J=8.0Hz), 4.5, 4.25(2xm, 2H, OCH$_2$), 3.0-3.45(m, NCH$_2$, H$_{11}$, H$_{22}$), 1.35, 1.05(2xs, (CH3)$_{15}$, (CH3)$_{18}$), 0.8, 0.62(2xd, (CH$_3$)$_{16}$, (CH$_3$)$_{17}$, J=6.8Hz) |

TABLE 3-continued

| R_EX | Example |
|---|---|
| (cyclohexane with methyl and dimethylhydrazone substituent) | Example 31<br>14-O-[(((E/Z)-Dimethylaminimino-cyclohexan-3-(R/S)-1-yl)-sulfanyl)acetyl]mutilin<br>($d_6$-DMSO): Diastereoisomers: 6.15, 5.1(2xm, $H_{19}$, $H_{20}$, $H_{21}$), 5.52(d, 1H, J=5.2Hz, $H_{14}$), 4.50(d, 1H, OH, J=5Hz), 3.45(t, 1H, $H_{11}$, J=5Hz), 3.3(m, 2H, $H_{22}$), 3.2, 2.8(2xm, 1H, CHS), 2.95, 1.85(2xm, 2H, $CH_2C$=N), 1.18, 1.45(2xs, $(CH3)_{15}$, $(CH3)_{18}$), 0.75, 0.88(2xd, $(CH_3)_{16}$, $(CH_3)_{17}$, J=5.4Hz) |
| (cycloheptane with methyl and hydroxyimino substituent) | Example 32a<br>14-O-[((E*-Hydroximino-cycloheptan-3-(R/S)-yl)-sulfanyl)-acetyl]mutilin<br>NMR($d_6$-DMSO): 10.35(s, 1H, HON=C), 6.15, 5.1(2xm, $H_{19}$, $H_{20}$, $H_{21}$), 5.52(d, 1H, J=5.2Hz, $H_{14}$), 4.5(d, 1H, OH, J=6.1Hz), 3.4(t, 1H, $H_{11}$, J=6.1Hz)), 3.3(m, 2H, $H_{22}$), 1.18, 1.45(2xs, $(CH3)_{15}$, $(CH3)_{18}$), 0.75, 0.88(2xd, $(CH_3)_{16}$, $(CH_3)_{17}$, J=5.4Hz).<br>Example 32b<br>14-O-[((Z*-Hydroximino-cycloheptan-3-(R/S)-yl)-sulfanyl)acetyl]mutilin<br>($d_6$-DMSO): 10.35(s, 1H, HON=C), 6.15, 5.1(2xm, $H_{19}$, $H_{20}$, $H_{21}$), 5.52(d, 1H, J=5.2Hz, $H_{14}$), 4.5(d, 1H, OH, J=5Hz)3.4(t, 1H, $H_{11}$, J=5Hz), 3.3(m, 2H, $H_{22}$), 3.05(m, 1H, SCH), 1.18, 1.45(2xs, $(CH3)_{15}$, $(CH3)_{18}$), 0.75, 0.88(2xd, $(CH_3)_{16}$, $(CH_3)_{17}$, J=5.4Hz) |
| (cycloheptane with diethylaminoethoxyimino substituent) | Example 33<br>14-O-{[(3-(2-Diethylamino-ethoxyimino)-cyclohept-(R/S)-yl)-sulfanyl]-acetyl}-mutilin hydrochloride(E/Z mixture)<br>(DMSO-$d_6$): 9.85(bs, 1H, $NH^+$), 6.15, 5.06, 5.03(3xm, $H_{19}$, $H_{20}$, $H_{21}$), 5.55(d, 1H, $H_{14}$, J=8.5Hz), 4.52, 4.53(2xd, 1H, 11-OH, J=6.2Hz), 4.28(m, 2H, $OCH_2$), 3.0-3.45(m, $NCH_2$, $H_{11}$, $H_{22}$), 1.35, 1.05 (2xs, $(CH_3)_{15}$, $(CH_3)_{18}$), 0.8, 0.62(2xd, $(CH_3)_{16}$, $(CH_3)_{17}$, J=6.8Hz) |
| (cycloheptane with pyrrolidinyl-ethoxyimino substituent) | Example 34<br>14-O-{[(3-(2-Pyrrolinine-1-yl-ethoxyimino)-cyclohept-1-(R/S)-yl)-sulfanyl]-acetyl}-mutilin hydrochloride(E/Z mixture)-<br>(DMSO-$d_6$): 10.2(bs, 1H, $NH^+$), 6.15, 5.08, 5.05(3xm, $H_{19}$, $H_{20}$, $H_{21}$), 5.58(d, 1H, $H_{14}$, J=8.3Hz), 4.53, 4.57(2xd, 1H, 11-OH, J=6.1Hz), 4.26(m, 2H, $OCH_2$), 3.0-3.45(m, $NCH_2$, $H_{11}$, $H_{22}$), 1.38, 1.08(2xs, $(CH_3)_{15}$, $(CH_3)_{18}$), 0.83, 0.64(2xd, $(CH_3)_{16}$, $(CH_3)_{17}$, J=6.8Hz). |
| (cycloheptane with piperidinyl-ethoxyimino substituent) | Example 35<br>14-O-{[(3-(2-Piperidine-1-yl-ethoxyimino)-cyclohept-(R/S)-yl)-sulfanyl]-acetyl}-mutilin in the form of a hydrochloride(E/Z mixture)<br>$^1$HNMR(DMSO-$d_6$): 10.0(bs, 1H, $NH^+$), 6.15, 5.06, 5.03(3xm, $H_{19}$, $H_{20}$, $H_{21}$), 5.55(d, 1H, $H_{14}$, J=8.4Hz), 4.5, 4.55(2xd, 1H, 11-OH, J=6.2Hz), 4.32(m, 2H, $OCH_2$), 2.8-3.5(m, $NCH_2$, $H_{11}$, $H_{22}$), 1.35, 1.05(2xs, $(CH_3)_{15}$, $(CH_3)_{18}$), 0.8, 0.62(2xd, $(CH_3)_{16}$, $(CH_3)_{17}$, J=6.8Hz) |

A compound of formula IC wherein
- $R_{1C}$ has the meaning of $R_{1A}$ as defined in formula $I_A$.
- $R_{2C}$ has the meaning of $R_{2A}$ as defined in formula $I_A$,
- the dotted line has the meaning as defined in formula $I_A$,
- $R_{4C}$ has the meaning of $R_{6A}$ as defined in formula $I_A$, and
- $R_{3C}$ is amino, $(C_{1-4})$alkylamino, di$(C_{1-4})$alkylamino, the residue of an amino acid, hydroxy, or $(C_{1-4})$alkoxy,
- e.g. preferably $R_{1C}$ is hydrogen, $R_{2C}$ is hydrogen, $R_{4C}$ is hydrogen, the dotted line is not present (single bond), and $R_{3C}$ is amino, di$(C_{1-4})$alkylamino, or the residue of an amino acid;
- e.g. including pleuromutilins which are selected from the group consisting of compounds of formula $I_{EX}$, wherein R_EX is as set out in TABLE 4 (¹H-NMR-data of the compounds described and obtained according, e.g. analogously, to a process as described in the examples are also indicated in TABLE 4):

TABLE 4

Example 36a
14-O-{[(3S,3aS,6S,6aR)-6-Amino-hexahydro-furo[3,2-b]furan-3-yl-sulfanyl]-acetyl}-mutilin in the form of a hydrochloride
(DMSO-$d_6$): 8.3(bs, 3H, $NH_3^+$), 6.15, 5.05, 5.02(3xm, $H_{19}$, $H_{20}$, $H_{21}$), 5.55(d, 1H, 8.2Hz, $H_{14}$), 4.65, 4.55(2xm, $H_{11}$-OH, H-3a', H6a'), 3.6-4.1(m, 5H, H-2', H-5', H-6'), 3.3-3.5(m, 4H, $H_{11}$, H-3', $H_{22}$), 1.35, 1.05(2xs, $(CH_3)_{15}$, $(CH_3)_{18}$), 0.8, 0.62(2xd, $(CH_3)_{16}$, $(CH_3)_{17}$, J=6.5Hz)

Example 36b
14-O-{[(3R,3aS,6S,6aR)-6-Amino-hexahydro-furo[3,2-b]furan-3-yl-sulfanyl]-acetyl}-mutilin-hydrochloride
(DMSO-$d_6$): 8.3(bs, 3H, $NH_3^+$), 6.15, 5.07, 5.03(3xm, $H_{19}$, $H_{20}$, $H_{21}$), 5.55(d, 1H, $H_{14}$, J=8.2Hz), 4.60, 4.7(2xm, H-3a', H6a'), 3.6-4.1(m, 5H, H-2', H-5', H-6'), 3.3-3.5(m, 4H, $H_{11}$, H-3', $H_{22}$), 1.35, 1.05, (2xs, $(CH_3)_{15}$, $(CH_3)_{18}$), 0.8, 0.62(2xd, $(CH_3)_{16}$, $(CH_3)_{17}$, J=6.9Hz)

Example 36c
14-O-{[(3S,3aS,6R,6aR)-6-Amino-hexahydro-furo[3,2-b]furan-3-yl-sulfanyl]-acetyl}-mutilin-hydrochloride
(DMSO-$d_6$): 8.25(bs, 3H, $NH_3^+$), 6.15, 5.06, 5.03(3xm, $H_{19}$, $H_{20}$, $H_{21}$), 5.55(d, 1H, $H_{14}$, J=8.4Hz), 4.60(m, 2H, H-3a', H6a'), 3.55-4.2(m, 5H, H-2', H-5', H-6'), 3.35-3.5(m, 4H, $H_{11}$, H-3', $H_{22}$), 1.35, 1.05(2xs, $(CH_3)_{15}$, $(CH_3)_{18}$), 0.8, 0.62(2xd, $(CH_3)_{16}$, $(CH_3)_{17}$, J=6.9Hz)

Example 37
14-O-{[(3S,3aS,6S,6aR)-6-Dimethylamino-hexahydro-furo[3,2-b]furan-3-ylsulfanyl]-acetyl}-mutilin in the form of a hydrochloride
(DMSO-$d_6$): 11.25(bs, 1H, $NH^+$), 6.15, 5.06, 5.03(3xm, $H_{19}$, $H_{20}$, $H_{21}$), 5.55(d, 1H, $H_{14}$, J=8.2Hz), 4.60(m, 1H, H3a'), 3.3-4.1(m, H-2', H-5', H-6', H-6a', $H_{11}$, H-3', $H_{22}$), 2.8, 2.7(2xd, 6H, $NH^+(CH_3)_2$, J=4.5Hz), 1.35, 1.05(2xs, $(CH_3)_{15}$, $(CH_3)_{18}$), 0.8, 0.62(2xd, $(CH_3)_{16}$, $(CH_3)_{17}$, J=6.9Hz)

Example 38a
14-O-{[(3S,3aS,6S,6aR)-6-((R)-Amino-3-methyl-butyrylamino)-hexahydro-furo[3,2-b]furan-3-ylsulfanyl]-acetyl}-mutilin in the form of a hydrochloride
(DMSO-$d_6$): 8.65(d, 1H, NH, J=8.2Hz), 7.8(bs, 3H, $NH_3^+$), 6.15, 5.07, 5.02(3xm, $H_{19}$, $H_{20}$, $H_{21}$), 5.55(d, 1H, 5.2Hz, $H_{14}$), 4.55, 4.45(2xm, 3H, $H_{11}$-OH, H-3a', H6a'), 3.6-4.2(m, 5H, H-2', H-5', H-6'), 3.4-3.5(m, 4H, $H_{11}$, H-3', $H_{22}$), 1.35, 1.05(2xs, $(CH_3)15$, $(CH_3)_{18}$), 0.88, 0.92(2xd, $(CH_3)_2CH$, J=6.8Hz), 0.8, 0.62(2xd, $(CH_3)_{16}$, $(CH_3)_{17}$, J=6.8Hz)

Example 38b
14-O-{[(3R,3aS,6S,6aR)-6-((R)-Amino-3-methyl-butyrylamino)-hexahydro-furo[3,2-b]furan-3-ylsulfanyl]-acetyl}-mutilin in the form of a hydrochloride
(DMSO-$d_6$): 8.8(d, 1H, NH, J=7.1Hz), 8.15(bs, 3H, $NH_3^+$), 6.15, 5.07, 5.03(3xm, $H_{19}$, $H_{20}$, $H_{21}$), 5.55(d, 1H, 7.9Hz, $H_{14}$), 4.6, 4.4(2xm, 2H, H-3a', H6a'), 3.6-4.2(m, 5H, H-2', H-5', H-6'), 3.2-3.5(m, 4H, $H_{11}$, H-3', $H_{22}$), 1.35, 1.05(2xs, $(CH_3)15$, $(CH_3)_{18}$), 0.89, 0.91(d, $(CH_3)_2CH$, J=6.8Hz), 0.8, 0.62(2xd, $(CH_3)_{16}$, $(CH_3)_{17}$, J=6.8Hz)

Example 38c
14-O-{[(3S,3aS,6R,6aR)-6-((R)-Amino-3-methyl-butyrylamino)-hexahydro-furo[3,2-b]furan-3-ylsulfanyl]-acetyl}-mutilin in the form of a hydrochloride
(DMSO-$d_6$): 8.4(d, 1H, NH, J=7.8Hz), 8.1(bs, 3H, $NH_3^+$), 6.15, 5.06, 5.02(3xm, $H_{19}$, $H_{20}$, $H_{21}$), 5.55(d, 1H, 8.2Hz, $H_{14}$), 4.6, 4.5(2xm, 2H, H-3a', H6a'), 3.6-4.4(m, 5H, H-2', H-5', H-6'), 3.3-3.5(m, 4H, $H_{11}$, H-3', H6a'), 3.6-4.4(m, 5H, H-2', H-5', H-6'), 3.3-3.5(m, 4H, $H_{11}$, H-3', $H_{22}$), 1.35, 1.05(2xs, $(CH_3)15$, $(CH_3)_{18}$), 0.94, 0.90(d, $(CH_3)_2CH$, J=6.8Hz), 0.8, 0.62(2xd, $(CH_3)_{16}$, $(CH_3)_{17}$, J=6.8Hz)

TABLE 4-continued

| $R_{EX}$ | |
|---|---|
| (structure shown) | Example 39a<br>14-O-{[(3S,3aS,6R,6aR)-6-Hydroxy-hexahydro-furo[3,2-b]furan-3-yl-sulfanyl]-acetyl}-mutilin<br>(DMSO-$d_6$): 6.15, 5.07, 5.03(3xm, $H_{19}$, $H_{20}$, $H_{21}$), 5.55(d, 1H, $H_{14}$, J=8.3Hz), 4.85(d, 1H, 6'-OH, J=6.4Hz), 4.5(d, 1H, 11-OH, J=6.1Hz), 3.65-4.45(m, H-3a', H-6a', H-2', H-5', H-6'), 3.3-3.45(m, H-5', $H_{11}$, H-3', $H_{22}$), 1.35, 1.05(2xs, (CH$_3$)$_{15}$, (CH$_3$)$_{18}$), 0.8, 0.62(2xd, (CH$_3$)$_{16}$, (CH$_3$)$_{17}$, J=6.9Hz)<br>Example 39b<br>14-O-{[(3R,3aS,6R,6aR)-6-Hydroxy-hexahydro-furo[3,2-b]furan-3-yl-sulfanyl]-acetyl}-mutilin<br>(DMSO-$d_6$): 6.15, 5.06, 5.03(3xm, $H_{19}$, $H_{20}$, $H_{21}$), 5.55(d, 1H, $H_{14}$, J=8.3Hz), 4.8(d, 1H, 6'-OH, J=5.7Hz), 4.5(d, 1H, 11-OH, J=6.1Hz), 3.7-4.45(m, H-3a', H-6a', H-2', H-5', H-6'), 3.2-3.5(m, H-5', $H_{11}$, H-3', $H_{22}$), 1.35, 1.05(2xs, (CH$_3$)$_{15}$, (CH$_3$)$_{18}$), 0.8, 0.62(2xd, (CH$_3$)$_{16}$, (CH$_3$)$_{17}$, J=6.8Hz)<br>Example 39c<br>14-O-{[(3S,3aS,6S,6aR)-6-Hydroxy-hexahydro-furo[3,2-b]furan-3-yl-sulfanyl]-acetyl}-mutilin<br>(DMSO-$d_6$): 6.1, 5.07, 5.02(3xm, $H_{19}$, $H_{20}$, $H_{21}$), 5.55(d, 1H, $H_{14}$, J=8.3Hz), 5.2(d, 1H, 6'-OH), 3.55-4.55(m, 11-OH, H-3a', H-6a', H-2', H-5', H-6'), 3.3-3.45(m, $H_{11}$, H-3', $H_{22}$), 1.35, 1.05(2xs, (CH$_3$)$_{15}$, (CH$_3$)$_{18}$), 0.8, 0.62(2xd, (CH$_3$)$_{16}$, (CH$_3$)$_{17}$, J=6.8Hz) |

14-O-(hydroxy- or oxo)-(heterocyclyl-sulfanylmethylcarbonyl)-pleuromutilins, wherein heterocyclyl is an aliphatic ring of 4 to 8 ring members, preferably 5 to 7, comprising one nitrogen as the heteroarom, e.g. a compound of formula (structure ID)

wherein
$R_{1D}$ has the meaning of $R_{1A}$ as defined above,
$R_{2D}$ has the meaning of $R_{2A}$ as defined above,
$R_{4D}$ has the meaning of $R_{6A}$ as defined above,
the dotted line has the meaning as defined above, and
$R_{3D}$ is aliphatic heterocyclyl of 4 to 8 ring members, and comprising one nitrogen atom as the heteroatom, or ($C_{4-8}$) cycloalkyl, which heterocyclyl or cycloalkyl is substituted by hydroxy or oxo;

e.g. preferably $R_{1D}$ is hydrogen or deuterium, $R_{2D}$ is hydrogen or deuterium, the dotted line is not present (single bond), $R_{3D}$ is as defined above, e.g. heterocyclyl has preferably 5 to 7 ring members, e.g. heterocyclyl is attached to the sulphur in a compound of formula ID via a carbon bond; such as hydroxypyrrolidino, hydroxypiperidino, oxo-perhydroazepinyl; and cycloalkyl is preferably ($C_{5-6}$)cycloalkyl, e.g. cyclopentanonyl, $R_{4D}$ is hydrogen or deuterium, e.g. including 14-O-(hydroxy- or oxo-hetrocyclyl-sulfanylmethylcarbonyl)-pleuromutilins, wherein heterocyclyl is an aliphatic ring of 4 to 8 ring members, preferably 5 to 7, comprising one nitrogen as the heteroarom, which are selected from the group consisting of pleuromutilins which are selected from the group consisting of compounds of formulae

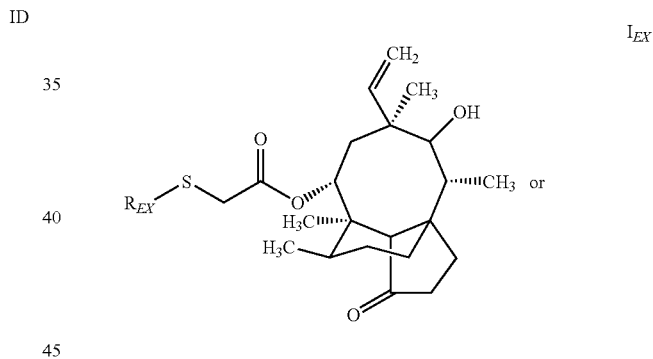

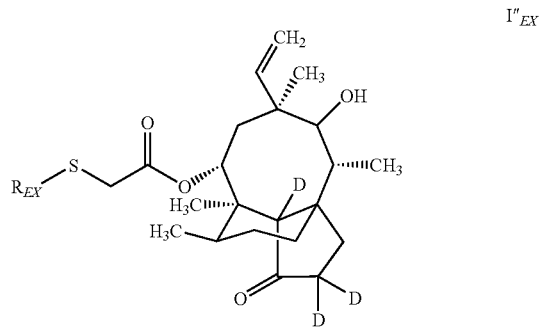

wherein $R_{EX}$ is as set out in TABLE 5 (the compounds of TABLE 5 are compounds of formula $I_{EX}$, with the exception of the compound of Example 41 which is a compound of formula $I''_{EX}$; $^1$H-NMR-data of the compounds described and obtained according, e.g. analogously, to a process as described in the examples are also indicated in TABLE 5):

TABLE 5

| R_EX | Example |
|---|---|
| (3-hydroxypyrrolidin-4-yl structure) R_EX—pyrrolidine with OH | Example 40<br>14-O-[(3-R*-Hydroxypyrrolidine-4-(R*)yl)-sulfanyl-acetyl]-mutilin and 14-O-[(3-S*-Hydroxypyrrolidine-4-(S*)yl)-sulfanyl-acetyl]-mutilin in the form of a hydrochloride(diastereoisomeric mixture)<br>(d-6-DMSO): 9.4, 9.65(2xb, 2H, NH$_2^+$), 3.6, 3.2(2xm, 4H, CH$_2$NCH$_2$), 4.45(m, 1H, CHO), 3.45-3.32(m, 3H, H$_{11}$H$_{22}$), 3.95(m, 1H, CHS), 1.18, 1.45(2xs, (CH3)$_{15}$, (CH3)$_{18}$), 0.75, 0.88(2xd, (CH$_3$)$_{16}$, (CH$_3$)$_{17}$, J=5.4Hz 0.98) |
| (3-hydroxypiperidin-4-yl) R_EX—piperidine with OH | Example 41<br>2,2,4-Trideutero-14-O-[((3-(S*)-hydroxy-piperidine-4-(S*)-yl)sulfanyl)-acetyl]mutilin in the form of a deuterochloride<br>(d-6-DMSO, 350K): 8.05(b, 3H, NH$_3^+$), 4.25-4.1(m, 3H, CH$_2$N, NHCHC═O), 3.75(m, 1H, CHO), 3.45-3.32(m, 3H, H$_{11}$H$_{22}$), 2.89(m, 1H, CHS), 1.18, 1.45(2xs, (CH3)$_{15}$, (CH3)$_{18}$), 0.9(m, 6H, CH(CH$_3$)$_2$), 0.75, 0.88(2xd, (CH$_3$)$_{16}$, (CH$_3$)$_{17}$, J=5.4Hz 0.98). The signals of the 2,2'- and 4-protons of the tricyclic moiety are missing in thast spectrum.<br>Mass Spectroscopy(MS): m/e: 496 |
| (3-hydroxypiperidin-4-yl, alt) R_EX—piperidine with OH, HN | Example 42<br>14-O-[(3R*-Hydroxypiperidin-4-(R*)yl)-sulfanyl-acetyl]mutilin in the form of a hydrochloride+14-O-[(3S*-Hydroxypiperidin-4-(S*)yl)-sulfanyl-acetyl]mutilin in the form of a hydrochloride<br>(d-6-DMSO, 350K): 8.05(b, 3H, NH$_3^+$), 4.25-4.1(m, 3H, CH$_2$N, NHCHC═O), 3.75(m, 1H, CHO), 3.45-3.32(m, 3H, H$_{11}$H$_{22}$), 2.89(m, 1H, CHS), 1.18, 1.45(2xs, (CH3)$_{15}$, (CH3)$_{18}$), 0.9(m,6H, CH(CH$_3$)$_2$), 0.75, 0.88(2xd, (CH$_3$)$_{16}$, (CH$_3$)$_{17}$, J=5.4Hz 0.98) |
| (azepan-2-one-4-yl) R_EX—azepanone | Example 43<br>14-O-[((Azepan-2-one-4-(R/S)-yl)-sulfanyl acetyl)]-mutilin<br>(d$_6$-DMSO): 6.15, 5.1(2xm, H$_{19}$, H$_{20}$, H$_{21}$), 5.52(d, 1H, J=5.2Hz, H$_{14}$), 3.4(m, 1H, H$_{11}$,), 3.3(m, 2H, H$_{22}$), 3.1(m, 2H, SCH, CHN), 1.18, 1.45(2xs, (CH3)$_{15}$, (CH3)$_{18}$), 0.75, 0.88(2xd, (CH$_3$)$_{16}$, (CH$_3$)$_{17}$, J=5.4Hz) |
| (3-oxo-cyclopentan-yl) R_EX—cyclopentanone | Example 44<br>14-O-{[(3-Oxo-cyclopentan-(R/S)-yl)-sulfanyl]-acetyl}-mutilin<br>(CDCl$_3$): 6.45, 5.35, 5.2(3xm, H$_{19}$, H$_{20}$, H$_{21}$), 5.8(d, 1H, H$_{14}$, J=8.4Hz), 3.6(m, 1H, SCH), 3.35(m, 1H, 11-OH), AB-system(v$_A$=3.25, v$_B$=3.17, 2H, H$_{22}$, J=14.8Hz), 2.65(m, ½H, H-2a'), 2.6(m, ½H, H-2a'), 1.45, 1.18(2xs, (CH$_3$)$_{15}$, (CH3)$_{18}$), 0.9, 0.75(2xd, (CH$_3$)$_{16}$, (CH$_3$)$_{17}$, J=6.8Hz) |

Compounds provided by the present invention, the formulae of which are as set out in TABLE 1 to TABLE 5, and compounds of formulae I$_A$, I$_B$, I$_C$, I$_D$, I$_{EX}$, I'$_{EX}$ and I"$_{EX}$ are herein designated as "SPECIAL compound(s) of (according to) the present invention". "The residue of an amino acid", whenever defined in any one of the SPECIAL compounds of the present invention includes that part of an amino acid, e.g. including natural and synthetic amino acids, e.g. valine and other amino acids as defined herein, most preferably valine; which remains if the hydroxy group from the carboxylic acid group is splitt off, e.g. In case of valine [HO—CO—CH(NH$_2$)—CH(CH$_3$)$_2$] the residue —CO—CH(NH$_2$)—CH(CH$_3$)$_2$.

In a SPECIAL compound of the present invention each single defined substitutent may be a preferred substituent, e.g. independently of each other substitutent defined. A SPECIAL compound of the present invention includes a compound in any form, e.g. in free form, in the form of a salt, in the form of a solvate and in the form of a salt and a solvate.

A salt of a SPECIAL compound of the present invention includes a pharmaceutically acceptable salt, e.g. including a metal salt or an acid addition salt. Metal salts include for example alkali or earth alkali salts; acid addition salts include salts of a compound of formula I with an acid, e.g. hydrogen fumaric acid, fumaric acid, naphthalin-1,5-sulphonic acid, phosphoric acid, tartaric acid, citric acid, hydrochloric acid, deuterochloric acid; preferably hydrochloric acid. A SPECIAL compound of the present invention in free form may be converted into a corresponding compound in the form of a salt; and vice versa. A SPECIAL compound of the present invention in free form or in the form of a salt and in the form of a solvate may be converted into a corresponding compound in free form or in the form of a salt in unsolvated form; and vice versa. A SPECIAL compound of the present invention may exist in the form of isomers and mixtures thereof; e.g. optical isomers, diastereoisomers, cis-, trans-conformers. A SPECIAL compound of the present invention may e.g. contain asymmetric carbon atoms and may thus exist in the form of diastereoisomeres and mixtures thereof, e.g. racemates. For example a SPECIAL compound of the present invention may comprise the residue of an amino acid. In such amino acid residue the carbon atom to which the amino group is attached may be an asymmetric carbon atom and the amino group attached may thus be in the R— or S-configuration. A SPECIAL compound of the present invention may comprise a cycloalkyl, e.g. attached to the sulfanyl group, which cycloalkyl may be further substituted, and said substitutents may exist in the cis or in the trans conformation. E.g., the carbon atom of a cycloalkyl group to which the sulfanylgroup is attached may be asymmetric, e.g. if said cycloalkyl is further substituted, and substituents attached to said cycloalkyl group may be in the R— or in the S-configuration.

E.g., a SPECIAL compound of the present invention also may comprise an oxime group. The hydroxgroup attached to the imino group may be in syn- or in anti-configuration. Isomeric mixtures may be separated as appropriate, e.g. according, e.g. analogously, to a method as conventional, to obtain pure isomers. The present invention includes a SPECIAL compound of the present invention In any isomeric form and in any isomeric mixture.

The present invention also includes tautomers of a SPECIAL compound of the present invention where such tautomers can exist.

Any compound described herein, e.g. a SPECIAL compound of the present invention, may be prepared as appropriate, e.g. according to a method as conventional, e.g. analogously, e.g. or as specified herein.

A SPECIAL compound of the present invention, e.g. a compound of formula

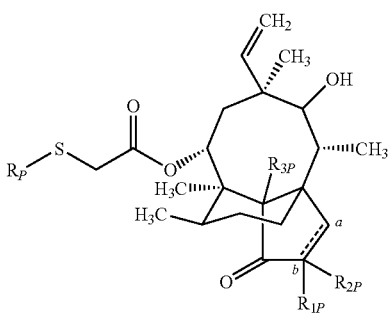

$I_P$ wherein
$R_{1P}$ has the meaning of $R_{1A}$ as defined above,
$R_{2P}$ has the meaning of $R_{2A}$ as defined above,
$R_{3P}$ has the meaning of $R_{6A}$ as defined above,
the dotted line has the meaning as defined above, and
$R_P$ has the meaning as set out in any one of the compounds of TABLE 1 to TABLE 5, and in a compound of formulae $I_A$, $I_B$, $I_C$, $I_D$, $I_{EX}$, $I'_{EX}$ and $I''_{EX}$,
may be prepared as appropriate, e.g. including a process comprising the steps of
a. reacting a compound of formula

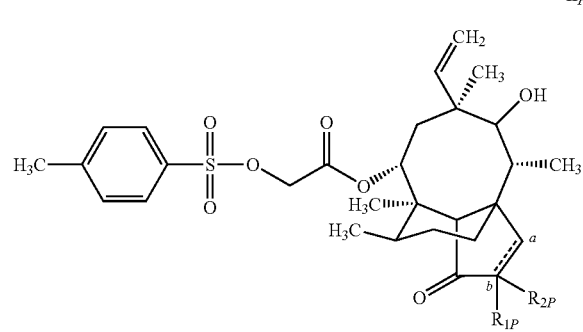

$II_P$ wherein $R_{1P}$ and $R_{2P}$ are as defined above, and the dotted line has the meaning as defined above,
with thiourea and subsequent reduction to obtain a compound of formula

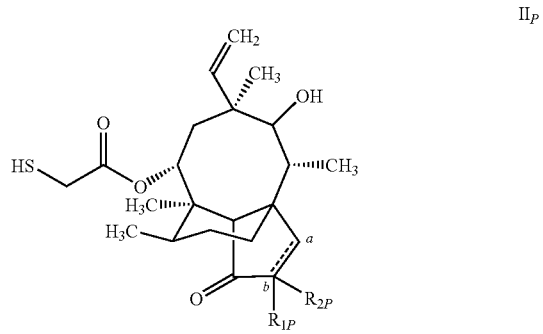

$II_P$ wherein $R_{1P}$ and $R_{2P}$ are as defined above,
b. reacting a compound of formula $II_P$ obtained in step a, with a compound of formula $R_P$—H wherein $R_P$ is as defined above, in a reactive form, e.g. a mesylate or a tosylate, optionally in a protected form,
to obtain a compound of formula $I_P$ (i.e. a SPECIAL compound of the present invention), or to obtain a pre-form of a compound of formula $I_P$,
c. optionally further reacting a pre-form obtained in step b. to obtain a compound of formula $I_P$, e.g. introducing deuterium to obtain a compound of formula $I_P$ wherein the subsitutents are as defined above, and
d. isolating a compound of formula $I_P$ obtained in step b. or in step c. from the reaction mixture.

$R_P$ is substituted ($C_{4-8}$)cycloalkyl, substituted phenyl, substituted aliphatic heterocyclyl, having 4 to 8 ring members and comprising as a heteroatom 1 or 2 nitrogen atoms, alkyl, substituted by (substituted) amino, alkyl substituted by heterocyclyl, or substituted, bicyclic aliphatic heterocyclyl, comprising in each ring 5 ring members and one oxygen heteroatom, e.g. including the meanings of $R_P$ in the SPECIAL pleuromutilins of the present invention, e.g. such as set out in any one of the compounds of TABLE 1 to TABLE 5, and in a compound of formulae $I_A$, $I_B$, $I_C$, $I_D$, $I_{EX}$, $I'_{EX}$ and $I''_{EX}$.

A process for the production of the SPECIAL compounds of the present invention may e.g. be carried out analogously to processes as set out in any of the patent references cited herein, e.g. analogously to a process for the production of compounds as described in patent literature cited herein, such as in WO0109095, WO0204414 and WO0222580, or as described herein. All patent references cited herein are introduced by reference, especially with respect to the claim scopes and meanings of the substituents, e.g. including the preferred meanings of the substituents, and with respect to production processes.

A pleuromutilin of the present invention includes the SPECIAL compounds of the present invention of formula $I_P$. A pleuromutilin of the present invention includes one or more, preferably one, pleuromutilins of the present invention, e.g. one pleuromutilin or a combination of different pleuromutilins of the present invention.

We have found that SPECIAL compounds of the present invention, including compounds of formula $I_P$, exhibit pharmacological activity similar to pleuromutilins in similar indications, e.g. as described in WO0109095, WO0204414 and WO0222580, e.g. in test systems similar as described in WO0109095, WO0204414 and WO0222580, and expectedly additionally in test systems as described herein. Compounds of formula $I_P$ are therefore useful as pharmaceuticals.

For pharmaceutical treatment, the appropriate dosage of a pleuromutilin will, of course, vary depending upon, for example, the chemical nature and the pharmakokinetic data of a pleuromutilin of the present invention used, the individual host, the mode of administration and the nature and severity of the conditions being treated. However, in general, for satisfactory results in larger mammals, for example humans, an indicated daily dosage is in the range from about 0.05 g to about 5.0 g, of a pleuromutilin of the present invention; conveniently administered, for example, in divided doses up to four times a day.

A pleuromutilin of the present invention may be administered by any conventional route, for example enterally, e.g. including nasal, buccal, rectal, oral administration; parenterally, e.g. including intravenous, intramuscular, subcutanous administration; or topically; e.g. including epicutaneous, intranasal, intratracheal administration;

e.g. in form of coated or uncoated tablets, capsules, injectable solutions or suspensions, e.g. in the form of ampoules, vials, in the form of creams, gels, pastes, inhaler powder, foams, tinctures, lip sticks, drops, sprays, or in the form of suppositories.

Pleuromutilins of the present invention may be administered in the form of a pharmaceutically acceptable salt, e.g. an acid addition salt or metal salt; or in free form; optionally in the form of a solvate. Pleuromutilins of the present invention in the form of a salt exhibit the same order of activity as the pleuromutilins of the present invention in free form; optionally in the form of a solvate.

A pleuromutilin of the present invention may be used for pharmaceutical treatment according to the present invention alone, or in combination with one or more other pharmaceutically active agents, e.g. such which show pharmaceutical activity against H.pylori infections, e.g. including antimicrobials, such as tetracycline, amoxicillin, metronidazole, clarithromycin, and mixtures of proton-pump inhibitors, such as omeprazole or lansoprazole, together with a second antimicrobial, e.g. amoxicillin or clarithromycin.

In another aspect the present invention provides the use of a pleuromutilin in combination with one or more other pharmaceutically active agents in the preparation of a medicament for the treatment of diseases mediated by Helicobacter pylori.

In another aspect the present invention provides a method for the treatment of diseases mediated by Helicobacter pylori, comprising administering to a subject in need of such treatment an effective amount of a pleuromutilin in combination with one or more other pharmaceutically active agents.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

A pharmaceutical composition comprising a pleuromutilin of the present invention further comprises at least one pharmaceutical excipient, e.g. appropriate carrier and/or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

Such compositions may be manufactured according, e.g. analogously to a method as conventional, e.g. by mixing, granulating, coating, dissolving or lyophilizing processes. Unit dosage forms may comprise, for example, from about 0.5 mg to about 1500 mg, such as 1 mg to about 500 mg.

Pleuromutilins of the present invention for administration in diseases mediated by H.pylori, may be administered in a similar mode and in similar dosages as other active agents in H.pylori treatment, such as amoxicillin or clarithromycin.

A pleuromutilin of the present invention is preferably selected from a compound of formula I-Valnemulin (Econor®) or a compound of formula $I_S$-WO0109095, e.g. a compound of formula

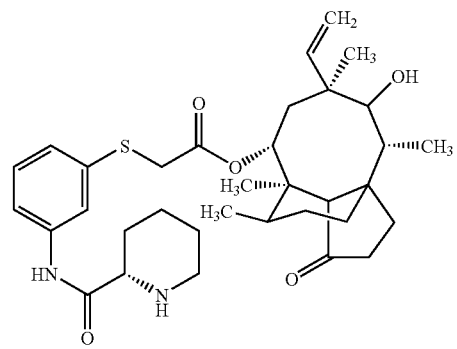

$I_{s1}$-WO0109095 or a compound of formula

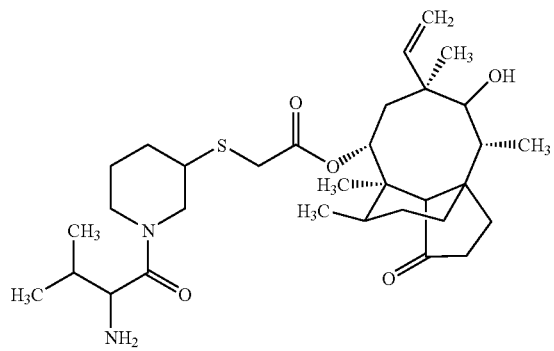

$I_{s2}$-WO0109095 e.g. in free form or in the form of a pharmaceutically acceptable salt.

Activity against strains of Helicobacter pylori is determined according to the Agar Dilution Method, using Mueller Hinton agar, supplementet with >2 week old horse blood (5% v/v), incubation at 35° C. for 3 days in a gas system-generated microaerobic atmosphere according to NCCLS recommendations, such as disclosed e.g. in "Methods for dilution antimicrobial susceptibility tests for bacteria that grow aerobically"—Fourth edition; approved standard. M7-A4 Vol. 17 No. 2 (1997) and M100-S9 Vol. 19 No. 1 (1999).

Pleuromutilins of the present invention show activity in such Test Methods against strains of H.pylori and are thus useful in the treatment of infections mediated, e.g. caused, by H.pylori. Pleuromutilins of the present invention surprisingly may be even active against resistant H.pylori strains, e.g. strains which are resistant against treatment with known pharmaceuticals useful in the treatment of diseases caused by H.pylori infections, e.g. metronidazole resistant strains.

In the following Examples all temperatures are in degree Centigrade and are uncorrected. The following abbreviations are used:

| | |
|---|---|
| BOC: tert.butoxyxcarbonyl | DCC: dicyclohexylcarbodiimide |
| DMF: N,N-dimethylformamide | DMSO: dimethylsulfoxide |
| EDC: N-(3-dimethylaminopropyl)-N'-ethylcarbodiimide hydrochloride | EtOH: ethanol |
| | MeOH: methanol |
| EtAc: ethyl acetate | RT: room temperature |
| HOBT: 1-hydroxybenzotriazole | TFA: trifluoroacetic acid |
| MS: mass spectroscopy | |
| TBAF: tetra-n-butylammonium fluoride | |
| THF: tetrahydrofurane | |

Chromatography is carried out on silica gel.

PREPARATION EXAMPLES

I. Preparation of (SPECIAL) Pleuromutilins of the Present Invention

Example I-A

14-O—[(N-(3-Methyl-2(R)-amino-butyryl)piperidine-3-yl)-sulfanylacetyl]-mutilin in the form of a hydrochloride I-AA) 14-O—[(N—BOC-Piperidin-3(S)-yl)-sulfanylacetyl]-mutilin Method 1:

532 mg of 22-O-tosyl-pleuromutilin are added to a solution of 217 mg of N—BOC-piperidine-3(S)-thiol and 112 mg potassium tert. butylate in 10 ml of THF, the mixture obtained is stirred for 3 hours, the mixture obtained is distributed between EtAc and brine, the organic phase obtained is dried, solvent is evaporated and the evaporation residue obtained is subjected to chromatography. 14-O—[(N—BOC-Piperidin-3(S)-yl)-sulfanylacetyl]-mutilin is obtained.

Method 2:

A solution of 1.97 g of 22-mercapto-pleuromutilin, 1.39 g of N—BOC-3(R)-methylsulfonyloxy-piperidine and 0.12 g of sodium in 50 ml of EtOH is heated to 90° for 12 hours, from the mixture obtained solvent is evaporated and the evaporation residue is subjected to chromatography. 14-O—[(N—BOC-piperidin-3-yl)-sulfanylacetyl]-mutilin is obtained.

$^1$H-MR(CDCl$_3$):6.45,5.35,5,2(3×m,H$_{19}$,H$_{20}$,H$_{21}$),5.74(d, 1H,5.2 Hz,H$_{14}$),3.35(d,1H,H$_{11}$,J=5.2 Hz), AB-system: 3.12, 3.18, J=14.7 Hz,H$_{22}$), 3.2,2.95,2.65,2.6(4×m,CH$_2$NCH$_2$), 2.85 (m,1H, SCH),1.18,1.45 (2×s,(CH3)$_{15}$,(CH3)$_{18}$), 0.75, 0.88(2×d,(CH$_3$)$_{16}$, (CH$_3$)$_{17}$,J=5.4 Hz)

I-AB) 14-O—[(N-(3-Methyl-2(R)-amino-butyryl)-piperidine-3-yl)-sulfanylacetyl]-mutilin in the form of a hydrochloride A solution of 280 mg of 14-O—[(N—BOC-piperidin-3-yl)-sulfanylacetyl]-mutilin in 20 ml of CH$_2$Cl$_2$ and 1 ml of TFA is stirred at RT for 30 minutes and from the mixture obtained solvent is evaporated. The evaporation residue obtained is treated with 40 ml of CH$_2$Cl$_2$, 55 mg of N-methylmorpholine, 110 mg of N—BOC—(R)-valine and 105 mg of DCC are added and the mixture obtained is stirred for 3 hours. From the mixture obtained precipitated dicyclohexylurea is filtered off and the filtrate obtained is subjected to chromatography. Purified 14-O—[(N-(3-Methyl-2(R)-amino-butyryl)-piperidine-3-yl)-sulfanylacetyl]-mutilin obtained is treated with TFA in CH$_2$Cl$_2$, solvent is evaporated and the evaporation residue obtained is treated with etheric HCl. 14-O—[(N-(3-Methyl-2(R)-amino-butyryl)-piperidine-3-yl)-sulfanylacetyl]-mutilin in the form of a hydrochloride is obtained.

$^1$H-NMR(d-6-DMSO,330K): 6.45,5.35,5,2(3×m,H$_{19}$,H$_{20}$,H$_{21}$), 5.74 (d,1H,5.2 Hz,H$_{14}$), 5.45 (d,1H,NH,J=7.8 Hz), 4.1 (m,1H,NHCHCO), 3.35 (d,1H,H$_{11}$,J=5.2 Hz), AB-system: 3.12,3.18, J=14.7 Hz,H$_{22}$), 3.2, 2.95, 2.65 ,2.6 (4×m, CH$_2$NCH$_2$), 2.8 (m,1H,SCH), 1.18,1.45 (2×s,(CH3)$_{15}$, (CH3)$_{18}$), 0.75,0.88 (2×d,(CH$_3$)$_{16}$,(CH$_3$)$_{17}$,J=5.4 Hz), 0.78.0.84 (2×d, (CH$_3$)$_2$CHJ=6.8 Hz)

Example I-B

14-O—[(N-(3Methyl-2(R)-amino-butyryl)-piperidine-3(S)-yl)-sulfanylacetyl]-2(S)-fluoro-mutilin in the form of a hydrochloride IBA) 14-O-(Tosyloxyacetyl)-2(S)-fluoro-mutilin To a solution of 500 mg of 14-O-(hydroxyacetyl)-2(S)-fluoro-mutilin (see e.g. Vyplel H., et al *J Fluorine Chem;* 23, 482 (1983)), in 5 ml of CH$_2$Cl$_2$ 450 mg of toluene sulfonic acid anhydride and 0.21 ml of pyridine are added and the mixture obtained is stirred for 4 hours at RT. The mixture obtained is diluted with CH$_2$Cl$_2$ and extracted with 1N HCl, aqueous NaHCO$_3$ and H$_2$O. The organic phase obtained is dried, solvent is evaporated and the evaporation residue is subjected to chromatography. 14-O-[tosyloxyacetyl]-2(S)-fluoro-mutilin is obtained.

IBB) 14-O—[(N-(3-Methyl-2(R)-amino-butyryl)-piperidine-3(S)-yl)-sulfanylacetyl]-2(S)-fluoro-mutilin in the form of a hydrochloride is obtained starting from 14-O-[tosyloxyacetyl]-2(S)-fluoro-mutilin analogously to the method of Example IAB). Characterisation data see TABLE 1, Example 12.

Example I-C

14-O-[(3-Guanidino-phenylsulfanyl)-acetyl]mutilin in the form of a hydrochloride ICA) 14-O-[(3-Amino-phenylsulfanyl)-acetyl]-mutilin A solution of 0.92 g of sodium and 5 g of 3-amino-thiophenol in 100 ml of dry EtOH is added to a solution of 21.3 g of 22-O-tosyl-pleuromutilin (see e.g. H.Egger et al., J.Antibiotics 29, 923 (1976)) in 250 ml of ethylmethylketone at 25° under careful temperature control. The mixture obtained is kept for 15 hours at 25°, filtered and the filtrate obtained is concentrated under reduced pressure and subjected to chromatography. 14-O-[(3-Amino-phenylsulfanyl)-acetyl]-mutilin is obtained. $^1$H-NMR(CDCl$_3$): 0.58(d, 3H, H$_{16}$, J=7.2 Hz), 0.81 (d, 3H, H$_{17}$, J=7.3 Hz),1.02 (s, 3H, H$_{18}$), 1.32 (s, 3H, H$_{15}$), ABX-system(ν$_A$=1.2, ν$_B$=1.88, H$_{13a}$, H$_{13b}$, J=16.1 Hz, J=9.1 Hz), 2.08(d,1H, H$_4$, J=2.1 Hz), ABXY-system (ν$_A$=2.23, V$_B$=2.19, H$_{2a}$, H$_{2b}$, J=16.2 Hz, J=9.1 Hz, J=1.8 Hz), 2.3(m,1H,H$_{10}$), 3.4 (d,1H,H$_{11}$, J=5.98 Hz), AB-system (ν$_A$=3.81, ν$_B$=3.89, 2H, H$_{22}$, J=14.1 Hz), 5.18(dd,1H, H$_{20a}$, J=17.5 Hz, J=1.6 Hz), 5.29(dd,1H, H$_{20b}$, J=11 Hz, J=1.6 Hz),5.51 (d,1H, H$_{14}$, J=8.3 Hz), 6.05 (dd,1H,H$_{19}$, J=11 Hz, J=17.5 Hz), 7.0 (m,1H, arom.H), 7.18 (m2H, arom.H), 7.3 t,1H, arom.H$_5$, J=8 Hz).

ICB)
14-O-[(3-Guanidino-phenylsulfanyl)-acetyl]mutilin in the form of a hydrochloride A solution of 2.4 g of 14-O-[(3-amino-phenylsulfanyl)-acetyl]mutilin, 1.5 g of cyanamide and 0.44 ml of HCl conc. in 20 ml of dioxane is stirred at room temperature for 28 hours. 14-O-[(3-Guanidino-phenylsulfanyl)-acetyl]mutilin in the form of a hydrochloride in crystalline form is obtained. Characterisation data see in TABLES above.

Exmple I-D

14-O-[(3R*-Hydroxypiperidin-4-(R*)yl)-sulfanyl-acetyl]mutilin and 14-O-[(3S*-Hydroxypiperidin-4-(S*)yl)-sulfanyl-acetyl]mutilin in the form of a hydrochloride (diastereoisomeric mixture)

1.06 g of pleuromutilin-22-O-tosylate dissolved in 1 ml of 2-butanone are slowly added to a solution of 466 mg of N—BOC-3-hydroxy-piperidin-4-thiol and 224 mg of potassium-tert. butylate in 20 ml of THF, the mixture obtained is stirred for 2 hours, the mixture obtained is distributed between brine and EtAc, extracted with 0.1N HCl, and the phases obtained are separated. The organic phase obtained is dried, and the evaporation residue obtained is subjected to chromatography. A mixture of 14-O-[(3R*-Hydroxypiperidin-4-(R*)yl)-sulfanyl-acetyl]mutilin and 14-O-[(3S*-Hydroxypiperidin-4-(S*)yl)-sulfanyl-acetyl]mutilin is obtained which is treated with etheric HCl to obtain the corresponding hydrochloride. Characterisation data see in TABLE 5, Example 42.

Example I-E 2,2,4-Trideutero-14-O-[((3-(S*)-hydroxy-piperidine-4-(S*)-yl)sulfanyl)-acetyl]mutilin in the form of a deuterochloride A solution of 300 mg of the compound obtained in Example ID in 30 ml dioxane with 5 ml of DCl (20% in $D_2O$) is kept for 6 days at 25°. From the mixture obtained solvent is evaporated and the concentration residue is subjected to lyophilization. 2,2,4-Trideutero-14-O-[((3-(S*)-hydroxy-piperidine-4-(S*)-yl)sulfanyl)-acetyl]mutilin in the form of a deuterochloride is obtained. Characterisation data see TABLE 5, Example 41.

Example I-F

14-O-[3-(R*)-((N—BOC—(R)-Valyl-amino-cyclohexan-1-(R*)-yl)sulfanyl)-acetyl]mutilin (a)
14-O-[3-(S*)-((N—BOC—(R)-Valyl-amino-cyclohexan-1-(S*)-yl)sulfanyl)-acetyl]mutilin (b)
14-O-[3-(S*)-((N—BOC—(R)-Valyl-amino-cyclohexan-1-(R*)-yl)sulfanyl)-acetyl]mutilin (c)
14-O-[3-(R*)-((N—BOC—(R)-Valyl-amino-cyclohexan-1-(S*)-yl)sulfanyl)-acetyl]mutilin (d)

2.66 g of pleuromutilin-22-O-tosylate dissolved in 10 ml THF are slowly added to a solution of 1.65 g of 3-(N—BOC—(R)-valyl-amino)-cyclohexane-(R/S)-thiol and 560 mg of potassium-tert. butylate in 25 ml of THF, the mixture obtained is stirred for 2 hours and distributed between brine and EtAc. The mixture obtained is extracted with 0.1N HCl , the organic phase obtained is dried, solvent is evaporated and the evaporation residue obtained is subjected to chromatography. Pure (a)   14-O-[3-(R*)-((N—BOC—(R)-Valyl-amino-cyclohexan-1-(R*)-yl)sulfanyl)-acetyl]mutilin
(b)   14-O-[3-(S*)-((N—BOC—(R)-Valyl-amino-cyclohexan-1-(S*)-yl)sulfanyl)-acetyl]mutilin
(c)   14-O-[3-(S*)-((N—BOC—(R)-Valyl-amino-cyclohexan-1-(R*)-yl)sulfanyl)-acetyl]mutilin, and
(d)   14-O-[3-(R*)-((N—BOC—(R)-Valyl-amino-cyclohexan-1-(S*)-yl)sulfanyl)-acetyl]mutilin is obtained. $^1$H-NMR($d_6$-DMSO):

(a): 6.5(d,1H,NH,J=8.1 Hz), 6.15, 5.1 (2×m,$H_{19}$,$H_{20}$,$H_{21}$), 5.52(d,1H,J=5.2 Hz,$H_{14}$), 3.4(m, 1H, $H_{11}$,), 3.55 (m,1H, CHN), 3.7 (m,α-valyl), 3.2 (m,2H,$H_{22}$), 2.7 (m,1H,SCH), 1.4 (s,9H, tert.butyl), 1.18,1.45(2×s,$(CH3)_{15}$,$(CH3)_{18}$), 0.75,0.88 (2×d,$(CH_3)_{16}$,$(CH_3)_{17}$, J=5.4 Hz).

(b): 6.15, 5.1 (2×m,$H_{19}$,$H_{20}$,$H_{21}$), 5.52(d,1H,J=5.2 Hz,$H_{14}$), 3.4(m,1H,$H_{11}$,), 3.55 (m,1H,CHN), 3.70 (m,α-valyl), 3.2 (m,2H,$H_{22}$), 2.7 (m,1H,SCH), 1.4 (s,9H,tert.butyl), 1.18, 1.45(2×s, $(CH3)_{15}$,$(CH3)_{18}$), 0.75,0.88 (2×d,$(CH_3)_{16}$, $(CH_3)_{17}$,J=5.4 Hz).

(c): 6.15, 5.1 (2×m,$H_{19}$,$H_{20}$,$H_{21}$), 5.52(d,1H,J=5.2 Hz,$H_{14}$), 3.4(m,1H,$H_{11}$,), 3.9 (m,1H,CHN), 3.75 (m,α-valyl), 3.2 (m,2H,$H_{22}$), 3.15 (m,1H,SCH), 1.4 (s,9H,tert.butyl), 1.18, 1.45(2×s, $(CH3)_{15}$,$(CH3)_{18}$), 0.75,0.88 (2×d,$(CH_3)_{16}$, $(CH_3)_{17}$,J=5.4 Hz).

(d): 6.15, 5.1 (2×m,$H_{19}$,$H_{20}$,$H_{21}$), 5.52(d,1H,J=5.2 Hz,$H_{14}$), 3.4(m,1H,$H_{11}$,), 3.9 (m, 1H,CHN), 3.70 (m,α-valyl), 3.2 (m,2H,$H_{22}$), 3.15 (m,1H,SCH), 1.4 (s,9H,tert.butyl), 1.18, 1.45(2×s, $(CH3)_{15}$,$(CH3)_{18}$), 0.75,0.88 (2×d,$(CH_3)_{16}$, $(CH_3)_{17}$,J=5.4 Hz).

Example I-G

14-O-[3-(R*)-((R)-Valyl-amino-cyclohexan-1-(R*)-yl)-sulfanyl)-acetyl]-mutilin and 14-O-[3-(S*)-((R)-Valyl-amino-cyclohexan-1-(S*)-yl)-sulfanyl)-acetyl]-mutilin in the form of a hydrochloride (mixture of trans-diastereoisomers)

620 mg of a 1:1 mixture of 14-O-[3-(R*)-((N—BOC—(R)-valyl-amino-cyclohexan-1-(R*)-yl)sulfanyl)-acetyl] mutilin and 14-O-[3-(S*)-((N—BOC—(R)-valyl-amino-cyclohexan-1-(S*)-yl sulfanyl)-acetyl]mutilin are dissolved in a mixture of 10 ml of dry etheric HCl and 10 ml of $CH_2Cl_2$. The mixture is stirred for 5 hours and a mixture of trans-diastereoisomers of 14-O-[3-(R*)-((R)-valyl-amino-cyclohexan-1-(R*)-yl)-sulfanyl)-acetyl]-mutilin of 14-O-[3-(S*)-((R)-valyl-amino-cyclohexan-1-(S*)-yl)-sulfanyl)-acetyl]-mutilin in the form of a hydrochloride is obtained and isolated. $^1$H-NMR($d_6$-DMSO,): Rotamer. 8.4 (m,1H, C═ONH), 8.15 (b,3H,$NH_3^+$), 6.15, 5.1 (2×m,$H_{19}$,$H_{20}$,$H_{21}$), 5.52(d,1H,J=5.2 Hz,$H_{14}$), 3.95 (m1H, $CHNH_3^+$,3.4(m,1H, $H_{11}$,), 3.55 (m,α-valyl), 3.2-3.3 (m,2H,$H_{22}$), 3.18 (m,1H, SCH), 1.18,1.45(2×s,$(CH3)_{15}$,$(CH3)_{18}$), 0.9 (m,6H,CH $(CH_3)_2$), 0.75,0.88 (2×d,$(CH_3)_{16}$,$(CH_3)_{17}$,J=5.4 Hz)

Example I-H

14-O-[3-(R*)-((R)-Valyl-amino-cyclohexan-1-(S*)-yl)-sulfanyl)-acetyl]-mutilin and 14-O-[3-(S*)-((R)-Valyl-amino-cyclohexan-1-(R*)-yl)-sulfanyl)-acetyl]-mutilin in the form of a hydrochloride (mixture of cis-diastereoisomers)

is obtained analagosouly to the method of Example I-G, but using a 1:1 mixture of 14-O-[3-(R*)-((N—BOC—(R)-valyl-amino-cyclohexan-1-(S*)-yl)sulfanyl)-acetyl]mutilin and 14-O-[3-(S*)-((N—BOC—(R)-valyl-amino-cyclohexan-1-(R*)-yl sulfanyl)-acetyl]mutilin as a starting material.

$^1$H-NMR(d$_6$-DMSO): Rotamers. 8.52 (m,1H,C=ONH), 8.2 (b,3H,NH$_3^+$), 6.15, 5.1 (2×m,H$_{19}$, H$_{20}$,H$_{21}$), 5.52(d,1H, J=5.2 Hz,H$_{14}$), 3.58 (m1H, CHNH$_3^+$, 3.4(m,1H,H$_{11}$,), 3.48 (m,α-valyl), 3.2-3.3 (m,2H,H$_{22}$), 2.75 (m,1H,SCH), 1.18, 1.45(2×s,(CH3)$_{15}$,(CH3)$_{18}$), 0.9 (m,6H,CH(CH$_3$)$_2$), 0.75,0.88 (2×d,(CH$_3$)$_{16}$,(CH$_3$)$_{17}$,J=5.4 Hz)

Example I-I

14-O-[((N—(R)-Valyl-azepan-4-(R/S)-yl)-sulfanyl acetyl)]-mutilin In the form of a hydrochloride I-IA) 4-(R/S)-(2,4,6-Trimethyl-benzyl-sulfanyl)-azepan-2-one A solution of 828 mg of 3-(R/S)-(2,4,6-trimethyl-benzyl-sulfanyl)-cyclohexanone-oxime and 570 mg of toluenesulfonylchloride in 5 ml of pyridine is stirred at RT for 4 hours and additional 2 hours at 60°. The mixture obtained is distributed between diluted sulfuric acid (2 ml H$_2$SO$_4$ conc. in 15 ml H$_2$O) and CH$_2$Cl$_2$, the organic phase obtained is dried, solvent is evaporated and the evaporation residue is subjected to chromatography. 4-(R/S)-(2,4,6-Trimethyl-benzyl-sulfanyl)-azepan-2-one is obtained. $^1$H-NMR(d-6-DMSO): 7.5 (m,1H,NHCO), 6.8 (s,2H,arom.H), 3.75 (s,2H, C$_6$H$_5$CH$_2$S—),3.2 (m, 1H,CHN), 3.1(m,3H, CH$_2$NH,CHS) AB-system: v$_A$=2.72,v$_B$=2.65(2H,CH2C=O, J=13.4 Hz, J=4.5 Hz) 2.13 2.15,2.3(9H, 3×CH$_3$)

I-IB) 4-(R/S)-(2,4,6-Trimethyl-benzyl-sulfanyl)-azepane 3.3 g of 4-(R/S)-(2,4,6-trimethyl-benzyl-sulfanyl)-azepan-2-one are added to a mixture of 15 ml of a 1M-solution of LiAlH$_3$ and 50 ml THF are added. The mixture obtained is heated for 1 hour at 80°, poured into 200 ml of a 20% aqueous NH$_4$Cl-solution and the mixture obtained is extracted with EtAc. The organic phase obtained is dried and solvent is evaporated. 4-(R/S)-(2,4,6-Trimethyl-benzyl-sulfanyl)-azepane is obtained.

I-IC) N—BOC-(4-(R/S)-(2,4,6-Trimethyl-benzyl-sulfanyl))-azepane

A solution of 2.63 g of 4-(R/S)-(2,4,6-trimethyl-benzyl-sulfanyl)-azepane, 2.18 g of BOC-anhydride and 1 g of triethylamine in 100 ml of THF is stirred at 25° for 12 hours and from the mixture obtained solvent is evaporated. The evaporation residue obtained is distributed between CH$_2$Cl$_2$ and 1M HCl. Solvent from the organic phase obtained is evaporated and the evaporation residue is subjected to chromatography. N—BOC-(4-(R/S)-(2,4,6-trimethyl-benzyl-sulfanyl))-azepane is obtained. $^1$H-NMR(d$_6$-DMSO): 6.8 (s,2H, arom.H), 3.75 (s,2H,C$_6$H$_5$CH$_2$S—),3.2-3.5(m,4H, CH$_2$NHCH$_2$), 2.9(m,1H,CHS), 2.13 2.15,2.3(9H, 3×CH$_3$)

I-IC) N—BOC-4-(R/S)-Azepan-thiol is obtained analogously to the method of Example II-D, but using appropriate starting materials.

I-ID) 14-O—[((N—BOC-Azepan-4-(R/S)-yl)-sulfanyl acetyl)]-mutilin

A solution of 1.06 g of pleuromutilin-22-O-tosylate dissolved in 10 ml THF is slowly added to a solution of 420 mg of N—BOC-(4-(R/S)-azepane-thiol and 220 mg of potassium-tert.butylate in 25 ml of THF and the mixture obtained is stirred for 2 hours. The mixture obtained is distributed between brine and EtAc, the mixture obtained is extracted with 0.1N HCl, the organic phase obtained is dried, solvent is evaporated and the evaporation residue obtained is subjected to chromatography. 14-O—[((N—BOC-azepan-4-(R/S)-yl)-sulfanyl acetyl)-mutilin is obtained. $^1$H-NMR(d$_6$-DMSO): 6.15, 5.1 (2×m,H$_{19}$,H$_{20}$,H$_{21}$), 5.52(d,1H,J=5.2 Hz,H$_{14}$), 4.52 (d,1H,OH,J=6.2 Hz)3.4(t,1H,H$_{11}$,J=6.2 Hz), 3.1-3.4 (m,6H, H$_{22}$,CH$_2$NCH$_2$), 2.9 (m,1H,SCH), 1.4 (s,9H,tert.butyl), 1.18, 1.45(2×s,(CH3)$_{15}$,(CH3)$_{18}$), 0.75,0.88 (2×d,(CH$_3$)$_{16}$, (CH$_3$)$_{17}$,J=5.4 Hz)

I-IE) 14-O-[((Azepan-4-(R/S)-yl)-sulfanyl acetyl)]-mutilin in the form of a hydrochloride 400 mg of 14-O—[((N—BOC-azepan-4-(R/S)-yl)-sulfanyl-acetyl)-mutilin are dissolved in a mixture of 10 ml of dry etheric HCl and 10 ml of CH$_2$Cl$_2$. The mixture obtained is stirred for 5 hours and 14-O-[((azepan-4-(R/S)-yl)-sulfanyl acetyl)]-mutilin in the form of a hydrochloride is isolated. Characterisation data see TABLE 1, Example 14.

I-IF) 14-O-[((N—(R)-Valyl-azepan-4-(R/S)-yl)-sulfanyl acetyl)]-mutilin in the form of a hydrochloride A mixture of 245 mg 14-O-[((azepan-4-(R/S)-yl)-sulfanyl acetyl)]-mutilin in the form of a hydrochloride, 110 mg of BOC—R-valin, 95 mg of EDC and 100 mg of triethylamine in 10 ml THF is stirred at RT for 2 hours. The mixture obtained is distributed between brine and EtAc, the organic phase obtained is dried, solvent is evaporated and the evaporation residue obtained is subjected to chromatography.

14-O—[((N—BOC—(R)-Valyl-azepan-4-(R/S)-yl)-sulfanyl acetyl)]-mutilin-hydrochloride is obtained. The BOC-protecting group is cleaved by treatment with 5 ml of etheric HCl and 14-O—[((N—(R)-Valyl-azepan-4-(R/S)-yl)-sulfanyl acetyl)]-mutilin in the form of a hydrochloride is obtained. Characterisation data see TABLE 1, Example 15.

Example I-J

14-O-[((Azepan-2-one-4-(R/S)-yl)-sulfanyl acetyl)]-mutilin is obtained analagously to the method of Example IAB), starting from 4-(R/S)-mercapto-azepan-2-one. Characterisation data see TABLE 5, Example 43.

Example I-K

14-O-{[(3-Oxo-cyclopentan-(R/S)-yl)-sulfanyl]-acetyl}-mutilin

A solution of 3.95 g of 14-mercapto-acetyl-mutilin in 5 ml of pyridine is treated with 0.81 g of cyclopent-2-enone and a catalytical amount of triethylamine. The mixture obtained is stirred for 3 hours at room temperature, diluted with EtAc and extracted with 1N HCl and H$_2$O. The organic phase obtained is dried, solvent is evaporated and the evaporation residue obtained is subjected to chromatography. 14-O-{[(3-oxo-cyclopentan-(R/S)-yl)-sulfanyl]-acetyl}-mutilin is obtained. Characterisation data see in TABLE 5, Example 44.

Example I-L

14-O-{[(3-Hydroxyimino-cyclopentan-(R/S)-yl)-sulfanyl]-acetyl}-mutilin (syn and anti forms)

3.88 g of 14-O-{[(3-oxo-cyclopentan-(R/S)-yl)-sulfanyl]-acetyl}-mutilin are stirred overnight with 566 mg of hydroxylamine hydrochloride and 1.13 ml of triethylamine in 40 ml of DMF. From the mixture obtained solvent is distilled off, the distillation residue obtained is taken up in EtAc and the mixture obtained is extracted with 0.1N HCl and brine. The organic phase obtained is dried and solvent is evaporated. A mixture of 14-O-{[(3-hydroxyimino-cyclo-pentan-(R/S)-yl)-sulfanyl]-acetyl}-mutilin in the syn*- and in the anti*-form is obtained which mixture is either separated by chromatography to obtain the pure syn- and the pure anti-forms, or is used in the form of the mixture obtained in further reaction steps. Characterisation data see TABLE 3, Example 24.

Example I-M

14-O-{[(3-(2-Diethylamino-ethoxyimino)-cyclopentan-(R/S)-yl)-sulfanyl]-acetyl}-mutilin in the form of a hydrochloride 200 mg of 14-O-{[(3-hydroxyimino-cyclopentan-(R/S)-yl)-sulfanyl]-acetyl}-mutilin and 70 mg of diethylaminoethylchloride hydrochloride are stirred in 5 ml of $CH_2Cl_2$, 90 mg of potassium tert butoxide are added and stirring is continued for 2 days at RT. From the mixture obtained solvent is evaporated, the evaporation residue is subjected to chromatography, the relevant chromatographic fractions obtained are distributed between $Et_2O$ and 0.1N HCl and the aqueous layer is lyophilized. 14-O-{[(3-(2-diethylamino-ethoxyimino)-cyclopent-(R/S)-yl)-sulfanyl]-acetyl}-mutilin hydrochloride (syn/anti mixture)is obtained. Characterisation data see TABLE 3, Example 26.

Example I-N

14-O-[(2-(R*)-((R)-Valyl)-amino-cyclohexan-1-(R*)-yl)-sulfanyl acetyl)]-mutilin-hydrochloride I-NA) 14-O-[((2-(R*)-Aminocyclohexan-1-(R*)-yl)-sulfanyl acetyl)]-mutilin 1.06 g of pleuromutilin-22-O-tosylate dissolved in 5 ml of THF are slowly added to a solution of 334 mg of 2-(R*)-aminocyclohexan-(R*)-thiol in the form of a hydrochloride (see e.g. G.Kavadias and R.Droghini, Can.J.Chem. 1978,56, 2743)and 92 mg sodium in 50 ml of EtOH, the mixture obtained is stirred for 2 hours, distributed between brine and EtAc, extracted with 0.1N HCl and dried. From the mixture obtained solvent is evaporated and the evaporation residue is subjected to chromatography. 14-O-[((2-(R*)-aminocyclohexan-1-(R*)-yl)-sulfanyl acetyl)]-mutilin is obtained. $^1$H-NMR($d_6$-DMSO): 6.15, 5.1 (2×m,$H_{19}$,$H_{20}$,$H_{21}$), 5.52(d,1H,J=5.2 Hz,$H_{14}$), 2.45(m,1H,CHNH), 3.21 (s,2H,$H_{22}$), 3.4 (d,1H, $H_{11}$,J=5 Hz), 2.55(m,1H,CHS), 1.18,1.45 (2×s, (CH3)$_{15}$,(CH3)$_{18}$), 0.9 (m,6H,CH(CH$_3$)$_2$), 0.75,0.88 (2×d, (CH$_3$)$_{16}$,(CH$_3$)$_{17}$,J=5.4 Hz).

I-NB) 14-O-[(2-(R*)-((R)-Valyl)-amino-cyclohexan-1-(R*)-yl)-sulfanyl acetyl)]-mutilin in the form of a hydrochloride A mixture of 245 mg of 14-O-[((2-(R*)-aminocyclohexan-1-(R*)-yl)-sulfanyl acetyl)]-mutilin, 110 mg of BOC—(R)-valin, 95 mg of EDC and 68 mg of HOBT in 10 ml of THF is stirred at RT for 2 hours. The mixture obtained is distributed between brine and EtAc, the organic phase obtained is dried, solvent is evaporated and the evaporation residue is subjected to chromatography. 14-O-[((2-(R*)-(N—BOC—(R)-Valyl)-amino-cylohexan-1-(R*)-yl)-sulfanyl acetyl)]-mutilin is obtained. The BOC-protecting group is cleaved by treatment with 5 ml of etheric HCl and 14-O-[(2-(R*)-((R)-valyl)-amino-cyclohexan-1-(R*)-yl)-sulfanyl acetyl)]-mutilin in the form of a hydrochloride is obtained. $^1$H-NMR($d_6$-DMSO): Diastereoisomers):8.45(m, 1H, NHC=O),8.1(b, 3H,NH$_3^+$), 6.15, 5;1 (2×m,$H_{19}$,$H_{20}$,$H_{21}$), 5.52(d,1H,J=5.2 Hz,$H_{14}$), 3.55 (m,1H, a-H-valyl),3.60(m,1H,CHNH), 3.26-3.35 (m,2H,$H_{22}$),3.4(m,1H, $H_{11}$), 4.5 (d,1H,OH, J=6.2 Hz), 2.6,2.75(2×m,1H,CHS), 1.25 (b,3H,CH$_3$CS), 1.18,1.45(2×s, (CH3)$_{15}$,(CH3)$_{18}$), 0.9 (m,6H,CH(CH$_3$)$_2$), 0.75,0.88 (2×d, (CH$_3$)$_{16}$,(CH$_3$)$_{17}$,J=5.4 Hz)

Example I-O

44-O-{[(3S,3aS, 6S,6aR)-6-Amino-hexahydro-furo[3,2-b]furan-3-ylsulfanyl]-acetyl}-mutilin hydrochloride I-OA) Toluene-4-sulfonic acid (3R,3aS,6R,6aR)-6-hydroxy-hexahydro-furo[3,2-b]furan-3-yl ester A solution of 5 g of (3R,3aS,6R,6aR)-hexahydro-furo[3,2-b]furan-3,6-diol in 50 ml of pyridine is stirred for 16 h with 7.8 g of toluenesulfonylchloride. From the mixture obtained solvent is distilled off and the distillation residue obtained is dissolved in EtAc and extracted with 1N HCl, saturated aqueous NaHCO$_3$-solution and H$_2$O. The organic layer obtained is dried, solvent is evaporated and the evaporation residue is subjected to chromatography. Toluene-4-sulfonic acid (3R, 3aS,6R,6aR)-6-hydroxy-hexahydro-furo[3,2-b]furan-3-yl ester is obtained. $^1$HNMR(DMSO-d$_6$): 7.8 (d,2H,Ar—H, J=8.6 Hz), 7.5 (d,2H,Ar—H,J=8.6 Hz), 4.8-4.9 (m,2H,H-3, 6-OH), 4.4 (dd,1H,H-3a,J=4.7 and 5.0 Hz), 4.2 (dd,1H,H-6a, J=4.7 and 4.8 Hz), 3.9-4.0 (m,1H,H-6), 3.7-3.8 (m,2H,H-2 and H-5), 3.6 (d,1H,H-2,J=9.3 and 7.1 Hz),3.2-3.4(m,1H,H-5), 2.4 (s, 3H, Ar—CH$_3$).

I-OB) (3R,3aR, 6S,6aR)-6-Azido-hexahydro-furo[3.2-b]furan-3-ol

A solution of 2.5 g of toluene-4-sulfonic acid (3R,3aS,6R, 6aR)-6-hydroxy-hexahydro-furo[3,2-b]furan-3-yl ester in 30 ml of DMF is heated with 0.8 g of sodium azide under reflux for 2 hours, solvent is distilled off and the distillation residue obtained is dissolved in EtAc and extracted with H$_2$O. The organic phase obtained is dried and solvent is evaporated. (3R,3aR, 6S,6aR)-6-azido-hexahydro-furo[3,2-b]furan-3-ol is obtained.

I-OC) {(3S,3aR,6R,6aR)-6-Hydroxy-hexahydro-furo[3.2-b]furan-3-yl}-carbamic acid tert-butyl ester To a solution of 1.5 g of (3R,3aR,6S,6aR)-6-azido-hexahydro-furo[3,2-b]furan-3-ol in 25 ml of dioxane 75 mg of palladium on charcoal (10%) are added and the mixture obtained is subjected to hydrogenation. The mixture obtained is filtered and stirred overnight with 3.2 ml of ethyidiisopropylamine and 4.1 g of (BOC)$_2$O. From the mixture obtained solvent is evaporated. The evaporation residue obtained is dissolved in EtAc and extracted with saturated aqueous sodium NaHCO$_3$-solution, 1N HCl and brine. The organic phase obtained is dried, solvent is evaporated and the evaporation residue obtained is subjected to chromatography. {(3S,3aR,6R,6aR)-6-hydroxy-hexahydro-furo[3,2-b]furan-3-yl}-carbamic acid tert-butyl ester is obtained. $^1$HNMR(DMSO-d$_6$): 7.1 (bs,1H,NH), 4.8 (d,1H,6-OH,J=10 Hz), 4.3 (dd,1H, H-6a,J=4.6 and 4.3 Hz), 4.27 (d,1H,H-3a,J=4.3 Hz), 4.0-4.1 (m,1H,H-6), 3.2-3.85 (m,5H,2×H-2, H-3, 2×H-5), 1.4 (s,9H, tert.butyl).

I-OD) Toluene-4-sulfonic acid (3R,3aS,6S,6aR)-6-tert-butoxycarbonylamino-hexahydro-furo[3,2-b]furan-3-yl ester A solution of 700 mg of {(3S,3aR,6R,6aR)-6-hydroxy-hexahydro-furo[3,2-b]furan-3-yl}-carbamic acid tert-butyl ester in 10 ml of pyridine is stirred for 16 hours with 785 mg of toluolsulfonylchloride, solvent is distilled off and the distillation residue is dissolved in EtAc and extracted with 1N HCl, saturated aqueous NaHCO$_3$-solution and H$_2$O. The organic layer obtained is dried and solvent is evaporated. Toluene-4-sulfonic acid (3R,3aS,6S,6aR)-6-tert-butoxycarbonylamino-hexahydro-furo[3,2-b]furan-3-yl ester is obtained.

I-OE) 14-O-{[(3S,3aS,6S,6aR)-6-tert-Butoxycarbonylamino-hexahydro-furo[3.2-b]furan-3-ylsulfanyl]-acetyl}-mutilin 267 mg of potassium tert.butoxide are added to a solution of 950 mg of toluene-4-sulfonic acid (3R,3aS,6S,6aR)-6-tert-butoxycarbonylamino-hexahydro-furo[3,2-b]furan-3-yl ester and 1032 mg of 14-mercapto-acetyl-mutilin in 20 ml of DMSO. The mixture obtained is stirred at 70° for 1 hour and distributed between EtAc and brine. The organic phase obtained is washed with H$_2$O, dried and solvent is evaporated. The evaporation residue obtained is subjected to chromatography. 14-O-{[(3S,3aS,6S,6aR)-6-tert-butoxycarbonyl-amino-hexahydro-furo[3,2-b]furan-3-ylsulfanyl]-acetyl}-mutilin is obtained. $^1$HNMR(DMSO-d$_6$): 7.1 (bs,1H,NH), 6.1, 5.05, 5.0 (3×m,H$_{19}$,H$_{20}$,H$_{21}$), 5.55 (d,1H,H$_{14}$, J=8.2 Hz), 4.5 (m,2H,H$_{11}$—OH,H-3a'), 4.4 (d, 1H, H-6a', J=4 Hz), 3.3-4.0 (m,9H,H-2',H-3',H-5',H-6',H$_{11}$,H$_{22}$), 1.36 (s,9H,tert-butyl), 1.34, 1.05 (2×s, (CH$_3$)$_{15}$, (CH$_3$)$_{18}$), 0.8, 0.62 (2×d (CH$_3$)$_{16}$, (CH$_3$)$_{17}$,J=6.8 Hz).

I-OF) 14-O-{[(3S,3aS,46S,6aR)-6-Amino-hexahydro-furo[3,2-b]furan-3-ylsulfanyl]-acetyl}-mutilin 950 mg of 14-O-{[(3S,3aS,6S,6aR)-6-tert-butoxycarbonylamino-hexahydro-furo[3,2-b]furan-3-ylsulfanyl]-acetyl}-mutilin are dissolved in 20 ml of CH$_2$Cl$_2$ and the mixture obtained is stirred for 2 hours with 3 ml of TFA. The mixture obtained is diluted with EtAc and extracted with saturated aqueous NaHCO$_3$-solution. The organic phase obtained is dried and solvent is evaporated. 14-O-{[(3S,3aS, 6S,6aR)-6-amino-hexahydro-furo[3,2-b]furan-3-ylsulfanyl]-acetyl}-mutilin is obtained.

I-OG) 14-O-{[(3S,3aS,6S,6aR)-6-Amino-hexahydro-furo3,2-b]furan-3-ylsulfany]-acetyl}-mutilin in the form of a hydrochloride 180 mg of 14-O-{[(3S,3aS,6S,6aR)-6-amino-hexahydro-furo[3,2-b]furan-3-ylsulfanyl]-acetyl}-mutilin are distributed between diethylether and 0.1N HCl. The aqueous layer obtained is lyophilized. 14-O-{[(3S,3aS,6S,6aR)-6-Amino-hexahydro-furo[3,2-b]furan-3-ylsulfanyl]-acetyl}-mutilin in the form of a hydrochloride is obtained. Characterisation data see in TABLE 4, Example 36a above.

Example I-P

14-O-{[(3S,3aS,6S,6aR)-6-((R)-Amino-3-methyl-butyrylamino)-hexahydro-furo[3,2-b]furan-3-ylsulfanyl]-acetyl}-mutilin in the form of a hydrochloride A solution of 400 mg of 14-O-{[(3S,3aS,6S,6aR)-6-amino-hexahydro-furo[3,2-b]furan-3-ylsulfanyl]-acetyl}-mutilin in 20 ml of CH$_2$Cl$_2$ is treated with 128 mg of N—Boc-(R)-valine, 147 mg of EDC, 104 mg of HOBT and the mixture obtained is stirred overnight at RT. The mixture obtained is diluted with CH$_2$Cl$_2$, extracted with H$_2$O, dried and solvent is evaporated. The evaporation residue obtained is subjected to chromatography on silica gel, relevant chromatographic fractions obtained are treated again with TFA in CH$_2$Cl$_2$, solvent is evaporated, the evaporation residue obtained is distributed between Et$_2$O and 0.1N HCl and the aqueous layer obtained is lyophilized. 14-O-{[(3S,3aS,6S,6aR)-6-((R)-2-amino-3-methyl-butyrylamino)-hexahydro-furo[3,2-b]furan-3-ylsulfanyl]-acetyl}-mutilin in the form of a hydrochloride is obtained. Characterisation data see in TABLE 5, Example 38a.

Example I-Q

14-O-[((3-(R/S)-Amino-cyclohexan-1-(R/S)-yl)-sulfanyl acetyl)]-mutilin in the form of a hydrochloride 10.6 g of pleuromutilin-22-O-tosylate dissolved in 10 ml of THF are slowly added to a solution of 5.2 g of N—BOC-3-(R/S)-mercapto-cyclohexylamin and 2.74 g of potassium-tert.butylate in 250 ml of THF. The mixture obtained is stirred for 2 hours, distributed between brine and EtAc, and extracted with 0.1N HCl. The organic phase obtained is dried, solvent is evaporated and the evaporation residue obtained is subjected o chromatography. 14-O-[((N—BOC-3(R/S)-amino-cyclohexan-1-(R/S)-yl)-sulfanyl acetyl)]-mutilin is obtained and is converted into 14-O-[((3-(R/S)-Amino-cyclohexan-1-(R/S)-yl)-sulfanyl acetyl)]-mutilin in the form of a hydrochloride by treatment with etheric HCl.
$^1$H-NMR(d$_6$-DMSO): 8.0 (b,3H,NH$_3$$^+$), 6.15, 5.1 (2×m, H$_{19}$,H$_{20}$,H$_{21}$), 5.52(d,1H,J=5.2 Hz,H$_{14}$), 3.4(m,1H,H$_{11}$,), 3.3 (m,2H,H$_{22}$), 2.9 (m,1H,NCH), 2.7(m,1H,CHS), 1.18,1.45 (2×s,(CH3)$_{15}$, (CH3)$_{18}$), 0.75,0.88 (2×d,(CH$_3$)$_{16}$,(CH$_3$)$_{17}$, J=5.4 Hz)

II. Preparation of Intermediates (Starting Materials) for the Preparation of a (SPECIAL) Pleuromutilin of the Present Invention Example II-A 14-Mercapto-acetyl-mutilin II-M) 14-O-[(Carbamimidoylsulfanyl)acetyl]mutilin-tosylate A solution of 15.2 g of thiourea and 106.4 g of pleuromutilin-22-O-tosylate in 250 ml of acetone is heated under reflux for 1.5 hours, solvent is removed and 100 ml of hexane are added. A precipitate forms, is filtrated off and dried.

14-O-[(carbamimidoylsulfanyl)acetyl]mutilin-tosylate is obtained.

II-AB) 14-Mercapto-acetyl-mutilin

A solution of 4.7 g of $Na_2S_2O_5$ in 25 ml of $H_2O$ is added to a solution of 12.2 g of 14-O-[(carbamimidoylsulfanyl)acetyl] mutilin-tosylate in a mixture of 20 ml of EtOH and 35 ml of $H_2O$ (warmed to ca. 90°). 100 ml of $CCl_4$ are added to the reaction mixture obtained and the mixture obtained is heated under reflux for ca. 2 hours. The two-phase system obtained is separated, the organic phase is dried and solvent is evaporated. 14-mercapto-acetyl-mutilin is obtained.

Example II-B
N—BOC-3(R)-methylsulfonyloxy-piperidine

II-BA) N—BOC-3(R)-Hydroxy-piperidine

A suspension of 3.48 g of 3-(R)-hydroxypiperidine, 8.72 g of di-tert.butyl-dicarbonat and 4 g of N-metyl-morpholine in 70 ml of dioxane is stirred for 18 hours at RT. From the mixture obtained solvent is evaporated and the evaporation residue obtained is dissolved in $CH_2Cl_2$ and extracted with 1N HCl. The organic phase obtained is dried and solvent is evaporated. N—BOC-3(R)-hydroxy-piperidine is obtained.

II-BB) N—BOC-3(R)-methylsulfonyloxy-piperidine

A solution of 5.08 g of N—BOC-3(R)-hydroxy-piperidine and 8.7 g of methanesulfonic acid anhydride in 100 ml pyridine is stirred at RT for 22 hours, pyridine is distilled off, the distillation residue is dissolved in $CH_2Cl_2$, the mixture obtained is extracted with 1N HCl, the organic phase obtained is dried, solvent is evaporated and the evaporation residue obtained is subjected to chromatography. N—BOC-3(R)-methylsulfonyloxy-piperidine is obtained.
$^1$H-NMR($CDCl_3$): 4.7(m,1H,$CHOSO_2CH_3$), 3.2-3.6(m, 4H,CHN), 3.0(s,3H,$CH_3SO_2$),1.4(m, 9H,tert.butyl).

Example II-C N—BOC-Piperidine-3(S)-thiol

II-CA) N—BOC-3-(S)-Thioacetoxy-piperidine

A solution of 2.2 g of N—BOC-3-(R)-hydroxy-piperidine in 10 ml of THF is added under argon and 1 ml of thiolacetic acid to a solution of 3.4 g of triphenylphosphine and 2.65 ml of azadicarbonic acid-isopropylate in 10 ml of THF. The mixture obtained is kept for 18 hours at 70°, solvent is evaporated and the evaporation residue obtained is subjected to chromatography. N—BOC-3-(S)-thioacetoxy-piperidine is obtained. $^1$H-NMR ($CDCl_3$): 3.78 (dd,1H,$NCH_2CHS$, J=3.1 Hz, J=13.3 Hz), 3.5-3.6 (m,2H, CHSC=O, $NCH_2CH_2$), 2.32 (s,3H,SC=O$CH_3$),1.46(s,9H, tert.butyl)

II-CB) N—BOC-Piperidine-3(S)-thiol

To a solution of 259 mg of N—BOC-3-(S)-thioacetoxy-piperidine in 10 ml of MeOH a solution of 262 mg of $NaSCH_3$ in 5 ml of MeOH is added and the mixture obtained is stirred for 2 hours, solvent is evaporated and the evaporation residue obtained is distributed between EtAc and aqueous HCl. Solvent from the organic phase obtained is evaporated. N—BOC-piperidine-3(S)-thiol is obtained. $^1$H-NMR($d_6$-DMSO): 2.6 (d,1H,SH, J=7.2 Hz), 2.9-2.7 (m,3H, $NCH_2$, CHS), 1.35 (b,9H,tert.butyl). MS(ESI)457 (2M+Na).

Example II-D 3-(N—BOC—(R)-Valyl-amino)-cyclohexane-(R/S)-thiol

II-DA) 3-(R/S)-(2,4,6-Trimethyl-benzyl-sulfanyl)-cyclohexanone

A solution of 3.32 g of 2,4,6-trimethyl-benzylmercaptane and 3.84 g of cyclohexen-3-one in 30 ml of pyridine is heated at 40° for 3 hours. The mixture obtained is poured into 200 ml of 1M HCl and the mixture obtained is extracted with $CH_2Cl_2$. The organic phase obtained is dried, solvent is evaporated and the evaporation residue is subjected to chromatography on silica gel. 3-(R/S)-(2,4,6-trimethyl-benzyl-sulfanyl)-cyclohexanone is obtained.
$^1$H-NMR($d_6$-DMSO): 6.8 (s,2H,arom.H), 3.8 (s,2H, $C_6H_5CH_2S$—), 3.3 (m,1H,CHS), 3.18 (dd,1H, CHC=NOH, J=4 Hz, 13.9 Hz), 2.65-2.8, 2.44-2.49(2×m,4H, $CH_2C$=O$CH_2$),2.15,2.3(9H,3×$CH_3$).

II-DB) 3-(R/S)-(2,4,6-Trimethyl-benzyl-sulfanyl)-cyclohexanone-oxime (syn and anti-forms)

A solution of 5.24 g of 3-(R/S)-(2,4,6-trimethyl-benzyl-sulfanyl)-cyclohexanone, 1.38 g of hydroxylamine in the form of a hydrochloride and 2 g of triethylamine in 50 ml of MeOH is stirred at 25° for 12 hours, the mixture obtained is poured into 200 ml of brine and the mixture obtained is extracted with $CH_2Cl_2$. The organic phase obtained is dried and solvent is evaporated. A mixture of the syn- and anti forms of 3-(R/S)-(2,4,6-trimethyl-benzyl-sulfanyl)-cyclohexanone-oxime is obtained which is subjected to chromatography. Pure syn- and pure anti-3-(R/S)-(2,4,6-trimethyl-benzyl-sulfanyl)-cyclohexanone-oxime is obtained.
$^1$H-NMR($d_6$-DMSO) of the syn-form: 10.3 (s,1H,OH), 6.8 (s,2H,arom.H), 3.75 (s,2H, $C_6H_5CH_2S$—), 2.88 (m,1H, CHS), 3.18 (dd,1H,CHC=NOH, J=4 Hz,13.9 Hz), 2.13 (dd, 1H, CHC=NOH, J=5.2 Hz,13.9 Hz), 2.15,2.3(9H, 3×$CH_3$).
$^1$H-NMR($d_6$-DMSO) of the anti-form: 10.3 (s,1H,OH), 6.8 (s,2H,arom.H), 3.75 (s,2H, $C_6H_5CH_2S$—), 2.92(m,1H, CHS), 2.58 (dd,1H,CHC=NOH, J=4 Hz,13.9 Hz), 2.15 (dd, 1H, CHC=NOH, J=4.2 Hz,13.6 Hz), 2.15,2.3(9H, 3×$CH_3$).

II-DC) 3-(R/S)-(2,4,6-trimethyl-benzyl-sulfanyl)-cyclohexyl-(R/S)-amine 2.7 g of 3-(R/S)-(2,4,6-Trimethyl-benzyl-sulfanyl)-cyclohexanone-oxime are added to a mixture of 20 ml of a 1M-solution of $LiAlH_3$ and 15 ml of dioxane, the mixture obtained is heated for 1 hour at 80° and the mixture obtained is poured into 200 ml of a 20% aqueous $NH_4Cl$-solution. The mixture obtained is extracted with EtAc, the organic phase obtained is dried and solvent is evaporated. 3-(R/S)-(2,4,6-trimethyl-benzyl-sulfanyl)-cyclohexyl-(R/S)-amine is obtained.

II-DC) 3-(N—BOC—(R)-Valyl-amino)-cyclohexan-1-(R/S)-yl-sulfanylmethyl-(2,4,6-trimethyl-benzol)

A mixture of 1.05 g of 3-(R/S)-(2,4,6-trimethyl-benzyl-sulfanyl)-cyclohexyl-(R/S)-amine, 870 mg of BOC—R-valine, 760 mg of EDC and 404 mg of triethylamine in 20 ml THF is stirred at RT for 2 hours. The mixture obtained is distributed between brine and EtAc, the organic phase obtained is dried, solvent is evaporated and the evaporation residue is subjected to chromatography. 3-(N—BOC—(R)-valyl-amino)-cyclohexan-1-(R/S)-yl-sulfanylmethyl-(2,4,6-trimethyl-benzol) is obtained. $^1$H-NMR(d$_6$-DMSO): Rotamers, 7.78, 7.3, 6.52 (3×d,2H,NH), J=7.9 Hz), 6.8, 6.82 (2×s, 2H, arom.H), 6.55 (m,1H,NHC=O),3.7 (m,1H,a-H-valyl), 3.6 (m,1H,NHCH), 2.75, 3.0 (2×m,1H, CHS), 1.39(s,9H, tert.butyl)

II-DD) 3-(N—BOC—(R)-Valyl-amino)-cyclohexane-(R/S)-thiol 10 ml ammonia are condensed at −70° within a solution of 600 mg of 3-(N—BOC—(R)-valyl-amino)-cyclohexan-1-(R/S)-yl-sulfanylmethyl-2,4,6-trimethyl-benzol in 15 ml of THF and sodium is added in portions until the solution remains deep blue. Solid NH$_4$Cl is added to the mixture obtained and the mixture obtained is allowed to warm up to RT, is flushed with nitrogen, the solid residue obtained is filtered off, the filtrate obtained is concentrated and subjected to chromatography on silica gel. 3-(N—BOC—(R)-Valyl-amino)-cyclohexane-(R/S)-thiol is obtained. $^1$H-NMR(d$_6$-DMSO): Rotamer, 7.75 (m,1H,NHCHC=O), 6.55 (m,1H, NHC=O),2.75 (m,1H,CHS), 2.58(d,1H,SH,J=6.6 Hz), 1.39 (s,9H,tert.butyl)

Analogously to the method as set out in Example II-D but using appropriate starting materials the following compounds are obtained:

Example II-D-1
N—BOC-3-(R/S)-mercapto-cyclohexylamin

Example II-D-2 4-(R/S)-Mercapto-azepan-2-one 4-(R/S)-(2,4,6-trimethyl-benzyl-sulfanyl)-azepan-2-one. $^1$H-NMR(d$_6$-DMSO): 6.15, 5.1 (2×m,H$_{19}$,H$_{20}$,H$_{21}$), 5.52(d, 1H,J=5.2 Hz,H$_{14}$), 3.4(m,1H,H$_{11}$,), 3.3 (m,2H,H$_{22}$), 2.99-3.12(b,2H,CH$_2$N), 3.18(m,1H,SCH), 2.7 (m,1H,C=OCH), 2.67(d,1H,SH,J=5.5 Hz), 2.58(d,1H,C=OCH,J=13.5 Hz), 1.18,1.45 (2×s,(CH3)$_{15}$,(CH3)18), 0.75,0.88 (2×d,(CH$_3$)$_{16}$, (CH$_3$)$_{17}$,J=5.4 Hz).

Example II-E N—BOC-3-(R/S)-(2,4,6-trimethyl-benzyl-sulfanyl)-cyclohexyl-(R/S)-amine A solution of 11 g of 3-(R/S)-(2,4,6-trimethyl-benzyl-sulfanyl)-cyclohexylamine, 9.15 g of BOC-anhydride and 4.2 g of triethylamine in 100 ml of THF is stirred at 25° for 12 hours, solvent is evaporated and the concentrated residue is distributed between CH$_2$Cl$_2$ and 1M HCl. From the organic phase obtained solvent is evaporated and the evaporation residue is subjected to chromatography. N—BOC-3-(R/S)-(2,4,6-trimethyl-benzyl-sulfanyl)-cyclohexyl-(R/S)-amine is obtained. $^1$H-NMR(d$_6$-DMSO): 6.81,(s,1H,NHCO), 6.8 (s,2H, arom.H), 3.75 (s,2H,C$_6$H$_5$CH$_2$S—),3.2 (m,1H,CHN), 2.70 (m,1H,CHS), 2.13 2.15,2.3(9H, 3×CH$_3$),1.4(s,9H,tert.butyl)

Example II-F Toluene-4-sulfonic acid (3S,3aS,6R,6aR)-6-hydroxy-hexahydro-furo[3,2-b]furan-3-yl ester and Toluene-4-sulfonic acid (3R,3aS,6S,6aR)-6-hydroxy-hexahydro-furan[3,2-b]furan-3-yl ester A solution of 8.76 g of (3S,3aS,6R,6aR)-hexahydro-furo [3,2-b]furan-3,6-diol in 80 ml of pyridine is stirred for 16 hours with 13.7 g of toluenesulfonylchloride, solvent is distilled off and the distillation residue is dissolved in EtAc and extracted with 1N HCl, saturated aqueous NaHCO$_3$-solution and H$_2$O. The organic layer obtained is dried, solvent is evaporated and the evaporation residue is subjected to chromatography. Toluene-4-sulfonic acid (3S,3aS,6R,6aR)-6-hydroxy-hexahydro-furo[3,2-b]furan-3-yl ester (a) and toluene-4-sulfonic acid (3R,3aS,6S,6aR)-6-hydroxy-hexahydro-furo [3,2-b]furan-3-yl ester (b) are obtained. $^1$HNMR(DMSO-d$_6$) of form (a): 7.8 (d,2H,Ar—H,J=8.2 Hz), 7.5 (d,2H,Ar—H, J=8.6 Hz), 4.95 (d,1H,6-OH), 4.8 (m, 1H, H-3), 4.42 (dd,1H, H-6a,J=4.6 and 4.8 Hz), 4.38 (d,1H,H-3a,J=4.6), 4.08 (m,1H, H-6), 3.8 (m,2H,2×H-2), 3.7, 3.25 (2×dd, 2H, 2×H-5), 2.4 (s, 3H, Ar—CH$_3$). $^1$HNMR(DMSO-d$_6$) of form (b): 7.8 (d,2H, Ar—H,J=8.6 Hz), 7.5 (d,2H,Ar—H,J=8.6 Hz), 5.15 (d, 6-OH, J=3.5), 4.9 (m, 1H, H-3), 4.45 (dd,1H,H-3a,J=4.3 and 4.8 Hz), 4.2 (d,1H,H6a,J=4.3), 4.0 (m,1H,H-6), 3.7 (m,3H, H-2 and 2×H-5), 3.5 (dd,1H,H-2,J=9.5 and 6.3 Hz), 2.4 (s, 3H, Ar—CH$_3$).

Example II-G
N—BOC-4-Hydroxy-piperidin-3-thiol, N—BOC-3-Hydroxy-piperidin-4-thiol A solution of 1 g of N—BOC-3,4-epoxy-piperidin, 1.9 g of triphenylsilylmercaptane and 0.7 ml of triethylamine in 12.5 ml of THF is stirred for 24 hours at 70°, and 1.7 g of TBAF and 0.9 ml acetic acid are added. The mixture obtained is stirred for 1 hour and distributed between brine and EtAc. The organic phase is dried, solvent is evaporated and the evaporation residue obtained is subjected to chromatography on silica gel. (a): N—BOC-4-Hydroxy-piperidin-3-thiol, and (b): N—BOC-3-hydroxy-piperidin-4-thiol are obtained.

$^1$H-NMR (CDCl$_3$) of (a): 4.45, 4.12, 2.8 (3×m,3H, CH$_2$NCH), 3.31 (dt, 1H, CHO, J=4.3 Hz,J=10 Hz), 2.65,2.6 (2×m,2H,CHN,CHS), 1.5(s,9H,tert.butyl).

$^1$H-NMR (CDCl$_3$) of (b): 4.25, 3.45 2.7, (3×m,3H, CH$_2$NCH), 3.2 (m,1H,CHO), 2.55(m,2H, NCH,CHS), 1.5(s, 9H,tert.butyl).

Test Example

In vitro Test Results of Pleuromutilins, Metronidazole and Tetracycline

Activity of TEST COMPOUNDS (TCs) against *H.pylori* strains ATCC 43504, 43526, 43629, 49503 and 51652 is determined according to the Agar Dilution Method, using Mueller Hinton agar, supplementet with >2 week old horse blood (5% v/v), incubation at 35° C. for 3 days in a gas system-generated microaerobic atmosphere according to NCCLS recommendations, such as disclosed in "Methods for dilution antimicrobial susceptibility tests for bacteria that grow aerobically "—Fourth edition; approved standard. M7-A4 Vol. 17 No. 2 (1997) and M100-S9 Vol. 19 No. 1(1999).

In vitro activity of the following TEST COMPOUNDS (TC) and of metronidazole and tetracycline Is determined:

TC-I: a compound of formula I-Valnemulin (Econor®)

TC-II: a compound of formula of formula I$_{s1}$-WO0109095

TC-III: a compound of formula of formula I$_{s2}$-WO0109095

Results of minimum inhibitory concentrations (MIC in µg/ml)) of TC-I, TC-II and TC-III and of metronidazole (MET) and tetracycline (TEC) in vitro tests against *Helicobacter pylori* (*H.pylori*) strains as set out in TABLE TEST are as set out in TABLE TEST below:

TABLE TEST

| Bacterial Strain/ ATCC number | MIC (µg/ml) | | | | |
|---|---|---|---|---|---|
| | TC-I | TC-II | TC-III | MET | TEC |
| H.pylori/43504 | 0.025 | <0.0125 | 0.025 | 128 | 0.4 |
| H.pylori/43526 | 0.05 | 0.05 | 0.05 | 4 | 0.4 |
| H.pylori/43629 | <0.0125 | <0.0125 | <0.0125 | 128 | 0.4 |
| H.pylori/49503 | <0.0125 | 0.025 | 0.025 | 4 | 0.2 |
| H.pylori/51652 | 0.025 | 0.025 | 0.025 | 2 | 0.2 |

The invention claimed is:

1. A method influencing the activity of *Helicobacter pylori*, comprising treating *Helicobacter pylori* with an effective amount of a pleuromutilin.

2. The method according to claim 1, wherein the pleuromutilin is selected from the group consisting of a pleuromutilin of formula

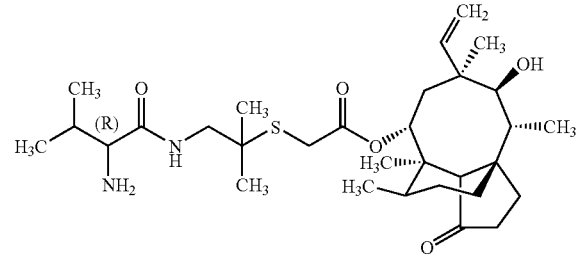

I-Valnemulin a pleuromutilin of formula

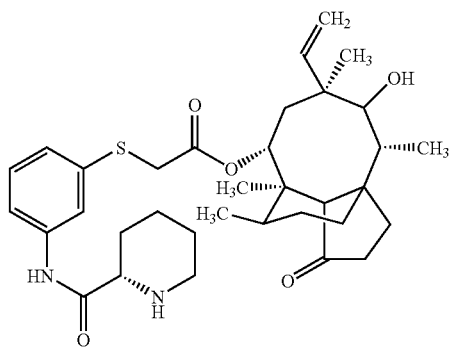

$I_{s1}$ and a pleuromutilin of formula

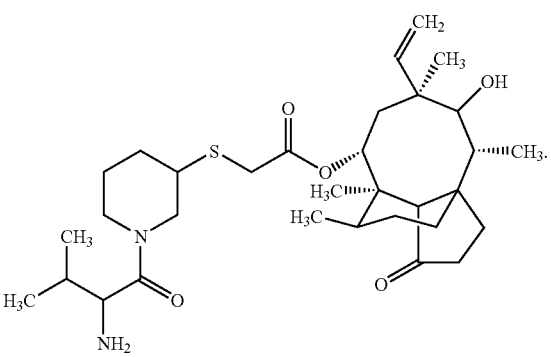

$I_{s2}$

3. The method according to claim 1, wherein the activity of *Helicobacter pylori* is decreased.

* * * * *